(12) United States Patent
Boedeker et al.

(10) Patent No.: US 9,327,019 B2
(45) Date of Patent: May 3, 2016

(54) ATTENUATED ENTEROHEMORRHAGIC E. COLI-BASED VACCINE VECTOR AND METHODS RELATING THERETO

(75) Inventors: Edgar C. Boedeker, Placitas, NM (US); Isaac Wyatt Byrd, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 0 days.

(21) Appl. No.: 13/378,116

(22) PCT Filed: Jun. 30, 2010

(86) PCT No.: PCT/US2010/040522
§ 371 (c)(1),
(2), (4) Date: Dec. 14, 2011

(87) PCT Pub. No.: WO2011/002836
PCT Pub. Date: Jan. 6, 2011

(65) Prior Publication Data
US 2012/0093870 A1 Apr. 19, 2012

Related U.S. Application Data

(60) Provisional application No. 61/221,612, filed on Jun. 30, 2009.

(51) Int. Cl.
*A61K 39/00* (2006.01)
*A61K 39/108* (2006.01)
(52) U.S. Cl.
CPC ....... *A61K 39/0258* (2013.01); *A61K 2039/522* (2013.01); *A61K 2039/523* (2013.01)
(58) Field of Classification Search
None
See application file for complete search history.

(56) References Cited

U.S. PATENT DOCUMENTS

| | | |
|---|---|---|
| 2003/0170264 A1 | 9/2003 | Turner et al. |
| 2008/0286310 A1 | 11/2008 | Zhu et al. |

FOREIGN PATENT DOCUMENTS

WO  WO 2008/133659  11/2008

OTHER PUBLICATIONS

Liu et al. Sheng Wu Gong Cheng Xue Bao. 23: 211-217, Mar. 2007.*
Liu et al. Sheng Wu Gong Cheng Xue Bao. 23: 211-217, Mar. 2007, English abstract.*
Byrd et al. In: Abstracts of the 109th General Meeting of the American Society for Microbiology, Philadelphia, PA, USA, #E-101, May 17-21, 2009.*
International Search Report received in PCT/US2010/040522, issued Mar. 28, 2011 by the Korean Patent Office; 3 pgs.
Written Opinion received in PCT/US2010/040522, issued Mar. 23, 2011 by the Korean Patent Office; 4 pgs.
International Preliminary Report on Patentability received in PCT/US2010/040522, issued Jan. 4, 2012 by the International Bureau of WIPO; 5 pgs.
Agin et al., "Protection against hemorrhagic colitis in an animal model by oral immunization with isogeneic rabbit enteropathogenic *Escherichia coli* attenuated by truncating intimin," *Infect.Immun*, 2005;73:6608-6619.
Altboum et al., "Attenuated *Shigella flexneri* 2a Delta guaBA strain CVD 1204 expressing enterotoxigenic *Escherichia coli* (ETEC) CS2 and CS3 fimbriae as a live mucosal vaccine against *Shigella* and ETEC infection," *Infect. Immun.*, 2001;69:31503158.
Altboum et al., "Genetic characterization and immunogenicity of coli surface antigen 4 from enterotoxigenic *Escherichia coli* when it is expressed in a *Shigella* live-vector strain," *Infect. Immun.*, 2003;71:1352-1360.
Baqar et al., "Murine intranasal challenge model for the study of *Campylobacter* pathogenesis and immunity," *Infect. Immun.*, 1996;64:4933-4939.
Barry et al., "Immune responses elicited against multiple enterotoxigenic *Escherichia coli* fimbriae and mutant LT expressed in attenuated Shigella vaccine strains," *Vaccine*, 2003;21:333-340.
Barry et al., "Immunogenicity of multivalent Shigella-ETEC candidate vaccine strains in a guinea pig model," *Vaccine*, 2006;24:3727-3734.
Black, R. E. "Epidemiology of travelers' diarrhea and relative importance of various pathogens," *Rev. Infect. Dis.*, 1990;12 Suppl 1:S73-S79.
Black, R. E. "The epidemiology of cholera and enterotoxigenic *Escherichia coli*," In A. L. R. M. J. Holmgren (ed.), *Development of vaccines and drugs against diarrhea*. 2007, Studentlitteratur, Lund, Sweden: p. 23-32.
Black et al., "Longitudinal studies of infectious diseases and physical growth of children in rural Bangladesh. I. Patterns of morbidity," *Am. J. Epidemiol.*,1982;115:305-314.
Brunder et al., "EspP, a novel extracellular serine protease of enterohaemorrhagic *Escherichia coli* O157:H7 cleaves human coagulation factor V.," *Mol. Microbiol.*, 1997;24:767-778.
Byrd and Cassels, "Mucosal immunization of BALB/c mice using enterotoxigenic *Escherichia coli* colonization factors CFA/I and CS6 administered with and without a mutant heat-labile enterotoxin," *Vaccine*, 2003;21:1884-1893.
Byrd and Cassels, "Intranasal immunization of BALB/c mice with enterotoxigenic *Escherichia coli* colonization factor CS6 encapsulated in biodegradable poly(DL-lactide-co-glycolide) microspheres," *Vaccine*, 2006;24:1359-1366.
Byrd and Cassels, "Long-term systemic and mucosal antibody responses measured in BALB/c mice following intranasal challenge with viable enterotoxigenic *Escherichia coli*," *FEMS Immunol. Med. Microbiol.*, 2006;46:262-268.

(Continued)

*Primary Examiner* — S. Devi
(74) *Attorney, Agent, or Firm* — Procopio, Cory, Hargreaves & Savitch LLP; Patrric J. Rawlins

(57) ABSTRACT

An attenuated enterohemorrhagic *E. coli*-based vaccine vector is disclosed. Enterotoxigenic *E. coli* colonization factor antigen 1 and the B subunit of *E. coli* heat labile toxin have been expressed in the attenuated enterohemorrhagic *E. coli* vector strain. Immunized animals are further protected against lethal and non lethal challenges with the enterotoxigenic *E. coli* strain. Immunization of mice with the vaccine construct induces mucosal antibody against both antigens, establishing the attenuated *E. coli* vector strain as a generally useful vector for presenting one or more antigens to a subject in a vaccine.

6 Claims, 38 Drawing Sheets

(56) References Cited

OTHER PUBLICATIONS

Byrd and Cassels, "The encapsulation of enterotoxigenic *Escherichia coli* colonization factor CS3 in biodegradable microspheres enhances the murine antibody response following intranasal administration," *Microbiology*, Mar. 1, 2006;152(3):779-786.

Byrd, W, and Kadis, S., "Preparation, characterization, and immunogenicity of conjugate vaccines directed against Actinobacillus pleuropneumoniae virulence determinants," *Infect. Immun.*, 1992;60:3042-3051.

Byrd et al., "Microencapsulated subunit vaccine approach to enterotoxigenic *Escherichia coli* and other mucosal pathogens," *Adv. Drug Deliv. Rev.*, 2005;57:1362-1380.

Byrd et al., "Pathogenicity and immune response measured in mice following intranasal challenge with enterotoxigenic *Escherichia coli* strains H10407 and B7A," *Infect. Immun.*, 2003;71:13-21.

Cantey and Inman, "Diarrhea due to *Escherichia coli* strain RDEC-1 in the rabbit: the Peyer's patch as the initial site of attachment and colonization," *J. Infect. Dis.*, 1981;143:440-446.

Cassels and Wolf, "Colonization factors of diarrheagenic *E. coli* and their intestinal receptors," *J. Ind. Microbiol.*, 1995;15:214-226.

Corbeil et al., "Killing of *Brucella* abortus by bovine serum," *Infect. Immun.*, 1988;56:3251-3261.

Cravioto et al. "Prospective study of diarrhoeal disease in a cohort of rural Mexican children: incidence and isolated pathogens during the first two years of life," *Epidemiol. Infect.*, 1988;101:123-134.

Cravioto et al., "Risk of diarrhea during the first year of life associated with initial and subsequent colonization by specific enteropathogens," *Am. J. Epidemiol.*, 1990;131:886-904.

Curtiss et al., "Avirulent *Salmonella typhimurium* delta cya delta crp oral vaccine strains expressing a *streptococcal* colonization and virulence antigen," *Vaccine*, 1988;6:155-160.

Curtiss et al., "Recombinant avirulent *Salmonella* vaccine strains with stable maintenance and high level expression of cloned genes in vivo," *Immunol. Invest*, 1989;18:583-596.

Darveau and Hancock, "Procedure for isolation of bacterial lipopolysaccharides from both smooth and rough *Pseudomonas aeruginosa* and *Salmonella typhimurium* strains," *J. Bacteriol.*, 1983;155:831-838.

de Lorimier et al., "Murine antibody response to intranasally administered enterotoxigenic *Escherichia coli* colonization factor CS6," *Vaccine*, 2003;21:2548-2555.

Donnenberg and Kaper, "Construction of an eae deletion mutant of enteropathogenic *Escherichia coli* by using a positive-selection suicide vector," *Infect. Immun.*, 1991;59:4310-4317.

Dorsey et al., "*Salmonella enterica* serotype Typhimurium MisL is an intestinal colonization factor that binds fibronectin," *Mol. Microbiol.*, 2005;57:196-211.

Duchet-Suchaux, M. "Suckling mouse model of enterotoxigenic *Escherichia coli* infection," In Zak O and M. A. Sands (ed.), *Handbook of Animal Models of Infection.*, 1999; Academic Press, San Diego: p. 241-253.

DuPont et al., "Pathogenesis of *Escherichia coli* diarrhea," *N. Engl. J. Med.*, 1971;285:1-9.

DuPont et al. "Comparative susceptibility of Latin American and United States students to enteric pathogens," *N. Engl. J. Med.*, 1976;295:1520-1521.

Evans et al., "Correlation between intestinal immune response to colonization factor antigen/I and acquired resistance to enterotoxigenic *Escherichia coli* diarrhea in an adult rabbit model," *Eur. J. Clin. Microbiol.*, 1982;1:178-185.

Eyles et al., "Intra nasal administration of poly-lactic acid microsphere co-encapsulated Yersinia pestis subunits confers protection from pneumonic plague in the mouse," *Vaccine*, 1998;16:698-707.

Eyles et al., "Analysis of local and systemic immunological responses after intra-tracheal, intra-nasal and intra-muscular administration of microsphere co-encapsulated Yersinia pestis sub-unit vaccines," *Vaccine*, 1998;16:2000-2009.
Freedman et al., "Milk immunoglobulin with specific activity against purified colonization factor antigens can protect against oral challenge with enterotoxigenic *Escherichia coli*," *J. Infect. Dis.*, 1998;177:662-667.
Gaastra and Svennerholm, "Colonization factors of human enterotoxigenic *Escherichia coli* (ETEC)," *Trends Microbiol.*, 1996;4:444-452.
Galan et al., "Cloning and characterization of the *asd* gene of *Salmonella typhimurium*: use in stable maintenance of recombinant plasmids in *Salmonella* vaccine strains," *Gene*,1990;94:29-35.
Galen et al., "Optimization of plasmid maintenance in the attenuated live vector vaccine strain *Salmonella typhi* CVD 908-htrA," *Infect. Immun.*,1999;67:6424-6433.
Galen et al., "Adaptation of the endogenous *Salmonella enterica serovar Typhi* clyA-encoded hemolysin for antigen export enhances the immunogenicity of anthrax protective antigen domain 4 expressed by the attenuated live-vector vaccine strain CVD 908-htrA," *Infect. Immun.*,2004;72:7096-7106.
Germanier, "Isolation and characterization of galE mutant Ty21a of *S. typhi*: a candidate for a live oral typhoid vaccine," *J. Infect. Dis.*, 1971;553-558.
Giron et al., "Simultaneous expression of CFA/I and CS3 colonization factor antigens of enterotoxigenic *Escherichia coli* by delta aroC, delta aroD *Salmonella typhi* vaccine strain CVD 908," *Vaccine*, 1995;13:939-946.
Helander et al., "Antibody responses in humans against coli surface antigen 6 of enterotoxigenic *Escherichia coli,*" *Infect. Immun.*, 1998;66:4507-4510.
Henderson et al., "Type V protein secretion pathway: the autotransporter story," *Microbiol. Mol. Biol. Rev.*, 2004;68:692-744.
Hone et al., "A chromosomal integration system for stabilization of heterologous genes in *Salmonella* based vaccine strains," *Microb. Pathog.*, 1998;5:407-418.
Hyams et al., "Diarrheal disease during Operation Desert Shield," *N. Engl. J. Med.*, 1991;325:1423-1428.
Klipstein et al., "Arousal of mucosal secretory immunoglobulin A antitoxin in rats immunized with *Escherichia coli* heat-labile enterotoxin," *Infect. Immun.*, 1982;37:1086-1092.
Koprowski et al., "Attenuated *Shigella flexneri* 2a vaccine strain CVD 1204 expressing colonization factor antigen I and mutant heat-labile enterotoxin of enterotoxigenic *Escherichia coli,*" *Infect. Immun.*, 2000;68:4884-4892.
Kuper et al., "The role of nasopharyngeal lymphoid tissue," *Immunol. Today*, 1992;13:219-224.
Levine et al., "New knowledge on pathogenesis of bacterial enteric infections as applied to vaccine development," *Microbiol. Rev.*, 1983;47:510-550.
Levine et al., "Immunity to enterotoxigenic *Escherichia coli,*" *Infect. Immun.*, 1979;23:729-736.
Mellies et al., "espC pathogenicity island of enteropathogenic *Escherichia coli* encodes an enterotoxin," *Infect. Immun.*, 2001;69:315-324.
Mynott et al., "Efficacy of enteric-coated protease in preventing attachment of enterotoxigenic *Escherichia coli* and diarrheal disease in the RITARD model," *Infect. Immun.*, 1991;59:3708-3714.
Nataro and Kaper, "Diarrheagenic *Escherichia coli,*" *Clin. Microbiol. Rev.*, 1998;11:142-201.
Nhieu and Sansonetti, "Mechanism of *Shigella* entry into epithelial cells," *Curr. Opin. Microbiol.*,1999;2:51-55.
Noriega et al., "Further characterization of delta aroA delta virG Shigella flexneri 2a strain CVD 1203 as a mucosal Shigella vaccine and as a live-vector vaccine for delivering antigens of enterotoxigenic *Escherichia coli,*" *Infect. Immun.*, 1996;64:23-27.
Oomen et al., "Structure of the translocator domain of a bacterial autotransporter," *EMBO J.*, 2004;23:1257-1266.
Qadri, et al., "Reduced doses of oral killed enterotoxigenic *Escherichia coli* plus cholera toxin B subunit vaccine is safe and immunogenic in Bangladeshi infants 6-17 months of age: dosing studies in different age groups," *Vaccine*, 2006;24:1726-1733.
Qadri et al., Safety and immunogenicity of an oral, inactivated enterotoxigenic *Escherichia coli* plus cholera toxin B subunit vaccine in Bangladeshi children 18-36 months of age. Vaccine, 2003;21:2394-2403.

(56) References Cited

OTHER PUBLICATIONS

Qadri et al., "Prevalence of toxin types and colonization factors in enterotoxigenic *Escherichia coli* isolated during a 2-year period from diarrheal patients in Bangladesh," *J. Clin. Microbiol.*, 2000;38:27-31.
Qadri et al., "Enterotoxigenic *Escherichia coli* in developing countries: epidemiology, microbiology, clinical features, treatment, and prevention," *Clin. Microbiol. Rev.*, 2005;18:465-483.
Ranallo et al., "Developing live Shigella vaccines using lambda Red recombineering," *FEMS Immunol. Med. Microbiol.*, 2006;47:462-469.
Ranallo et al., "Construction and Characterization of Bivalent *Shigella flexneri* 2a Vaccine Strains SC608(pCFAI) and SC608(pCFAI/LTB) that express antigens from Enterotoxigenic *Escherichia coli,*" *Infect Immun.*, Jan. 2005;73(1):258-267.
Ranallo et al., "Immunogenicity and characterization of WRSF2G11: a second generation live attenuated *Shigella flexneri* 2a vaccine strain," *Vaccine*, 2007;25:2269-2278.
Rao et al., "High disease burden of diarrhea due to enterotoxigenic *Escherichia coli* among rural Egyptian infants and young children," *J. Clin. Microbiol.*, 2003;41:4862-4864.
Reid et al., "Preclinical evaluation of microencapsulated CFA/II oral vaccine against enterotoxigenic *E. coli,*" *Vaccine*, 1993;11:159-167.
Ruiz-Olvera et al., "Display and release of the Plasmodium falciparum circumsporozoite protein using the autotransporter MisL of *Salmonella enterica,*" *Plasmid*, 2003;50:12-27.
Ruiz-Perez et al., "Expression of the *Plasmodium falciparum* immunodominant epitope (NANP)(4) on the surface of *Salmonella enterica* using the autotransporter MisL," *Infect. Immun.*, 2002;70:3611-3620.
Russmann et al., "Delivery of epitopes by the *Salmonella* type III secretion system for vaccine development," *Science*, 1998;281:565-568.
Sansonetti et al., "Rupture of the intestinal epithelial barrier and mucosal invasion by *Shigella flexneri,*" *Clin. Infect. Dis.*, 1999;28:466-475.
Savarino et al., "Introductory evaluation of an oral, killed whole cell enterotoxigenic *Escherichia coli* plus cholera toxin B subunit vaccine in Egyptian infants," *Pediatr. Infect. Dis. J.*,2002;21:322-330.
Shaheen et al., "Phenotypic profiles of enterotoxigenic *Escherichia coli* associated with early childhood diarrhea in rural Egypt," *J. Clin. Microbiol.*, 2004;42:5588-5595.
Stein-Streilein, J. "Immunobiology of lymphocytes in the lung," *Reg Immunol.*,1988;1:128-136.
Svennerholm et al., "Development of oral vaccines against enterotoxigenic *Escherichia coli* diarrhea," *Vaccine*, 1989;7:196-198.
Svennerholm and Steele, "Progress in enteric vaccine development," *Best Practice & Res. Clin. Gastroenterol.*, 2004; 421-445.
Tacket et al. "Enteral immunization and challenge of volunteers given enterotoxigenic *E. coli* CFA/II encapsulated in biodegradable microspheres," *Vaccine*, 1994;12:1270-1274.
Taylor et al., "Etiology and epidemiology of travelers' diarrhea in Asia," *Rev. Infect. Dis.*,1986; 8 Suppl 2:S136-S141.
Turbyfill et al., "Isolation and characterization of a *Shigella flexneri* invasin complex subunit vaccine," *Infect. Immun.*, 2000;68:6624-6632.
Turner et al., "Construction and characterization of genetically defined aro omp mutants of enterotoxigenic *Escherichia coli* and preliminary studies of safety and immunogenicity in humans," *Infect. Immun.*, 2001;69:4969-4979.
Van De Verg et al., "Antibody and cytokine responses in a mouse pulmonary model of *Shigella flexneri* serotype 2a infection," *Infect. Immun.*, 1995;63:1947-1954.
Velarde and Nataro, "Hydrophobic residues of the autotransporter EspP linker domain are important for outer membrane translocation of its passenger," *J. Biol. Chem.*, 2004;279:31495-31504.
Vray et al., "A new quantitative fluorimetric assay for phagocytosis of bacteria," *Scand. J. Immunol.*, 1980;11:147-153.
Wolf, M. K., "Occurrence, distribution, and associations of O and H serogroups, colonization factor antigens, and toxins of enterotoxigenic *Escherichia coli,*" *Clin. Microbiol. Rev.*, 1997;10:569-584.
Wolf et al., "Characterization of enterotoxigenic *Escherichia coli* isolated from U.S. troops deployed to the Middle East," *J. Clin. Microbiol.*, 1993; 31:851-856.
Wu et al., "Nasal lymphoid tissue (NALT) as a mucosal immune inductive site," *Scand. J. Immunol.*, 1997;46:506-513.
Wu et al., "Development of antibody-secreting cells and antigen-specific T cells in cervical lymph nodes after intranasal immunization," *Infect. Immun.*, 1997;65:227-235.
Wu et al., "Induction of antibody-secreting cells and T-helper and memory cells in murine nasal lymphoid tissue," *Immunology*, 1996;88:493-500.
Yamamoto et al., "Enteroadhesion fimbriae and enterotoxin of *Escherichia coli*: genetic transfer to a streptomycin-resistant mutant of the *galE* oral-route live-vaccine *Salmonella typhi* Ty21a," *Infect. Immun.*, 1985;50:925-928.
Zhu et al., "Complete nucleotide sequence and analysis of the locus of enterocyte Effacement from rabbit diarrheagenic *Escherichia coli* RDEC-1," *Infect. Immun.*, 2001;69:2107-2115.
Zhu et al., "Towards a vaccine for attaching/effacing *Escherichia coli*: a LEE encoded regulator (ler) mutant of rabbit enteropathogenic *Escherichia coli* is attenuated, immunogenic, and protects rabbits from lethal challenge with the wild-type virulent strain," *Vaccine*, 2006;24:3845-3855.
Zhu et al., "LEE-encoded regulator (Ler) mutants elicit serotype-specific protection, but not cross protection, against attaching and effacing *E. coli* strains," *Vaccine*, 2007;25:1884-1892.
Zhu et al., "Delivery of heterologous protein antigens via hemolysin or autotransporter systems by an attenuated ler mutant of rabbit enteropathogenic *Escherichia coli,*" *Vaccine*, 2006;24:3821-3831.
Zychlinsky et al., "In vivo apoptosis in Shigella flexneri infections," *Infect. Immun.*, 1996; 64:5357-5365.
"Toward a live Attenuated *Escherichia coli* Vaccine for Enterotoxigenic *Escherichia coli* (ETEC)," Poster at the VISN Forum in Phoenix, AZ from Apr. 8-9, 2009.1 page.
"Toward a live Attenuated *Escherichia coli* Vaccine for Enterotoxigenic *Escherichia coli* (ETEC)," abstract No. E-101. Abstract at the 109th General Meeting of the American Society for Microbiology (ASM) in Philadelphia, PA From May 17-21, 2009. 1 page.
"Toward a live Attenuated *Escherichia coli* Vaccine for Enterotoxigenic *Escherichia coli* (ETEC)," Poster at the 109th General Meeting of the American Society for Microbiology (ASM) in Philadelphia, PA from May 17-21, 2009, Wednesday May 20, 2009, poster No. 328. 1 page.
"Toward a live Attenuated *Escherichia coli* Vaccine for Enterotoxigenic *Escherichia coli* (ETEC)," Five-page extended abstract at the Cholera and Other Bacterial Enteric Infections 44th Annual Joint Panel Meeting (United States- Japan Cooperative Medical Science Program) in San Diego, CA, Oct. 12-14, 2009. 5 pages.
"A live Attenuated *Escherichia coli* Vaccine Provides Immunoprotection Against Enterotoxigenic *Escherichia coli* (ETEC)," Poster at the VISN Forum in Albuquerque, NM from May 6-7, 2010. 1 page.
"A live Attenuated *Escherichia coli* Vaccine Provides Immunoprotection Against Enterotoxigenic *Escherichia coli* (ETEC) in a Mouse model," abstract No. E-1653, Abstract at the 110th General Meeting of the American Society for Microbiology (ASM) in San Diego, CA From May 23-27, 2010. 1 page.
"A live Attenuated *Escherichia coli* Vaccine Provides Immunoprotection Against Enterotoxigenic *Escherichia coli* (ETEC) in a Mouse model," Poster at the 110th General Meeting of the Amercian Society for Microbiology (ASM) in San Diego, CA from May 23-27, 2010, Poster No. 436. 1 page.
A Live Attenuated *Escherichia coli* Vaccine Reduces Intestinal Fluid Accumulation and Intestinal Bacterial Colonization in BALB/c Mice Following Challenge with ETEC H10407 Wild-Type Strain. Abstract at the 111th General Meeting of the American Society for Microbiology (ASM) in New Orleans, LA. May 21-24, 2011. 1 page.

(56) References Cited

OTHER PUBLICATIONS

A Live Attenuated *Escherichia coli* Vaccine Reduces Intestinal Fluid Accumulation and Intestinal Bacterial Colonization in BALB/c Mice Following Challenge with ETEC H10407 Wild-Type Strain. Poster at the 111$^{th}$ General Meeting of the American Society for Microbiology (ASM) in New Orleans, LA. May 21-24, 2011. 1 page.

Mice Immunized Intranasally with an Attenuated *Escherichia coli* Strain Expressing the Enterotoxigenic *Escherichia coli* (ETEC) CFA/I Antigen Shoed a Reduced Inflammatory Response Following ETEC Wild-Type Challenge. Abstract at the 112$^{th}$ General Meeting of the American Society for Microbiology (ASM) in San Francisco, CA. Jun. 16-19, 2012. 1 page.

Mice Immunized Intranasally with an *Escherichia coli* Strain Expressing the Enterotoxigenic *Escherichia coli* (ETEC) CFA/I and LThK63 Antigens Showed a Reduced Inflammatory Responses Following ETEC Wild-Type Challenge. Poster at the 112$^{th}$ General Meeting of the American Society for Microbiology (ASM) in San Francisco, CA. Jun. 16-19, 2012. 1 page.

Boedeker, E. C. "Prospects for oral vaccines for enteric bacterial infections," In S. R. Targan and F. Shanahan (ed.), *Immunology and immunopathology of the liver and gastrointestinal tract*, 1990; Igaku-Shoin, New York: 435-457.

Brewer, N. R., "Respiratory physiology," In H. L. Foster, J. D. Small, and J. G. Fox (ed.), *The Mouse in Biomedical Research: Normative Biology, Immunology, and Husbandry*, 1983, Academic Press, New York. p. 252.

McGhee et al., "Mucosal vaccines: an overview," In P. L. Ogra, J. Mestecky, M. E. Lamm, W. Strober, J. Bienenstock, and J. R. McGhee (ed.)., p. 741-757. Academic Press, San Diego, 1999.

McQueen et al., "Pili in microspheres protect rabbits from diarrhea induced by *E. coli* strain RDEC-1," *Vaccine*, 1993;11:201-206.

Tacket and Levine, "Vaccines against enterotoxigenic *Escherichia coli* infections. Part ii: Live oral vaccines and subunit (purified fimbriae and toxin subunit) vaccines," In M. M. W. G. C. K. J. B. C. G. S. Levine (ed.), *New generation vaccines*, second edition. Marcel Dekker, New York, 1997; p. 875-883.

Tribble et al., "ETEC and enteric vaccines," In E. C. Z. J. N. Jong (ed.), *Travelers' vaccines*, BC Deker, London, 2004; p. 275-297.

Wolf et al., "Use of the human challenge model to characterize the immune response to the colonization factors of enterotoxigenic *Escherichia coli* (ETEC)," *Proceedings of the Thirty-fifth U. S. Japan Conference on Cholera and Other Bacterial Enteric Infections*, 1999; 189-193.

\* cited by examiner

Figure 1

| | ZCR533 EHEC Vector Strain | ETEC H10407 Wild-Type Strain | EHEC (CFA/I) Vaccine Strain | EHEC (CFA/I+mLT) Vaccine Strain |
|---|---|---|---|---|
| Transmission Electron Microscopy (TEM)[1] | 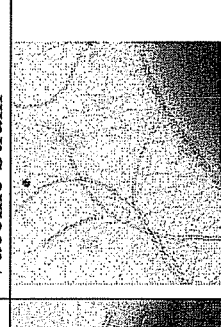 |  | 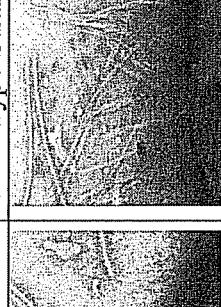 | 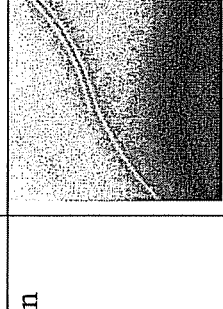 |
| Hemagglutination of type A RBCs[2] | Negative | Positive | Positive | Positive |
| Bacterial Surface Hydrophobicity,[3] | Hydrophilic [4 M $(NH_4)_2SO_4$] | Hydrophobic [0.08 M $(NH_4)_2SO_4$] | Hydrophobic [0.08 M $(NH_4)_2SO_4$] | Hydrophobic [0.08 M $(NH_4)_2SO_4$] |
| Phadebact® ETEC-LT Assay[4] | LT Negative | LT Positive | LT Negative | LT Positive |
| In vitro[5] Plasmid Stability | N/A | N/A | Plasmid retained by 70% of bacteria after 100 generations | Plasmid retained by 70% of bacteria after 100 generations |
| In vivo[6] Plasmid Stability | N/A | N/A | Plasmid stable for 10 days after IN dosing | Plasmid stable for 10 days after IN dosing |

ATTENUATED ENTEROHEMORRHAGIC *E. COLI*-BASED VACCINE VECTOR AND METHODS RELATING THERETO

CROSS-REFERENCE TO RELATED APPLICATION

This application is the §371 U.S. National Stage of International Application No. PCT/US2010/040522, filed 30 Jun. 2010, which claims priority to U.S. Provisional Patent Application Ser. No. 61/221,612, filed Jun. 30, 2009, each of which is hereby incorporated by reference in its entirety.

GOVERNMENT FUNDING

The present invention was made with government support under Grant No. 1R21AI079711-01A1, awarded by the National Institutes for Health, National Institutes of Allergy and Infectious Disease. The Government has certain rights in this invention.

BACKGROUND

Enterotoxigenic *E. coli* (ETEC) are important bacterial pathogens causing worldwide morbidity and mortality. Enterotoxigenic *E. coli* infections are important causes of death in infants and children under the age of five in developing countries. Illness caused by an enterotoxigenic *E. coli* infection is often self-limiting, lasting about one week. However, the illness can range from a mild diarrhea with little to no dehydration to a very severe and potentially fatal cholera-like disease, particularly in infants. Enterotoxigenic *E. coli* are also the leading cause of diarrhea in travelers to high-risk areas.

Despite our good understanding of ETEC virulence factors, and although several potential ETEC vaccines tested in volunteer trials and field studies, no safe and effective vaccine is yet available for at-risk individuals. Safe and effective ETEC vaccines would have a considerable public health impact worldwide in infants in developing countries, in travelers from industrialized countries to the developing world, and for the military.

SUMMARY OF THE INVENTION

The present invention relates to methods that involve administering a composition to a subject in order to induce the subject to generate an immune response against one or more components of the composition. Generally, the method includes administering to a subject a composition that includes an attenuated enterohemorrhagic *E. coli* (EHEC) in an amount effective to induce the subject to generate an immune response against at least one immunogen expressed by the attenuated EHEC.

In some embodiments, the immunogen can be an immunogen naturally expressed by the EHEC. In other embodiments, the immunogen can be a heterologous immunogen such as, for example, an immunogen that is expressed by the attenuated EHEC from a heterologous polynucleotide that encodes the heterologous immunogen. Thus, in some embodiments, the attenuated EHEC can include a heterologous polynucleotide that encodes one or more heterologous immunogens.

In some embodiments, the wild-type of the attenuated EHEC can a pathogen to the subject.

In some embodiments, administering the composition to the subject can protect the subject against challenge by an enterotoxigenic *E. coli*.

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 1 shows properties of wild-type ETEC, ZCR533 EHEC vector, ZCR533-CFA/I vaccine construct, and ZCR533-CFA/I+mLT vaccine construct. [1]TEM with Negative staining (0.25% Phosphotungstic acid) reveals CFA/I fimbriae surrounding the ZCR533(pGA-CFA/I) and ZCR533 (pGA-CFA/I-truLThK63) vaccine strains as well as the ETEC H10407 wild-type strain. No fimbriae were seen on the vector. [2]The CFA/I-expressing vaccine strains and wild-type H10407 strain induce characteristic mannose resistant agglutination of type A red blood cells not seen with ZCR53 alone. [3]The characteristic hydrophobicity of CFA/I protein (believed to aid in overcoming repulsive electrostatic forces during adherence) was seen in WT H10407 and with the EHEC CFA/I and EHEC CFA/I-mLT constructs. Expressing CFA/I, which aggregated at low salt concentrations [0.08M]. The ZCR522 vector, which has hydrophilic surface properties only aggregated at a high salt concentration [4 M]. [4]Only the ZCR533(pGA-CFA/I-truLThK63) vaccine and the ETEC H10407 wild-type strains were positive for LT production, whereas, the ZCR533 vector and ZCR533(pGA-CFA/I) vaccine non-LT producing strains were negative in this assay. [5]In vitro stability of the plasmids containing a kanamycin resistance marker were shown by serial passage of the strains in broth for ten 12 hour periods (100 generations) followed by plating of the strains on agar with and without kanamycin. [6]In vivo stability of the plasmids was shown following intranasal administration of the vaccines to mice by culturing lung contents daily for ten days and quantitating the numbers of kanamycin-resistant CFUs.

DETAILED DESCRIPTION OF ILLUSTRATIVE EMBODIMENTS

Figure 2:
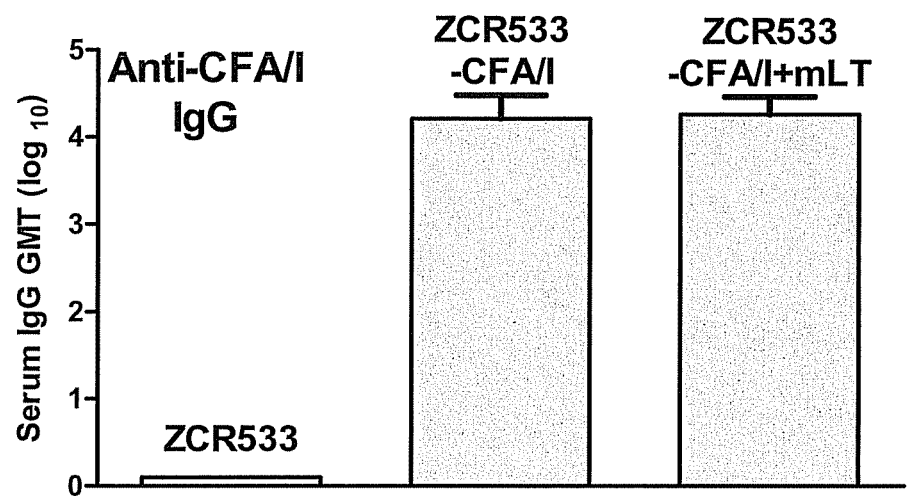
FIG. 2 shows serum α-CFA/I IgG response in mice vaccinated with ZCR533 EHEC vector, the ZCR533-CFA/I vaccine construct, or the ZCR533-CFA/I+mLT vaccine construct.
Figure 3:
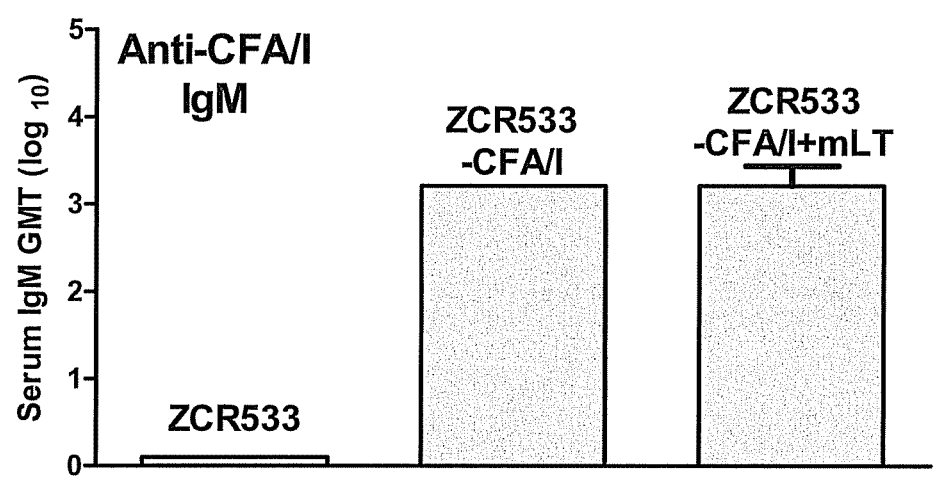
FIG. 3 shows serum α-CFA/I IgM response in mice vaccinated with ZCR533 EHEC vector, the ZCR533-CFA/I vaccine construct, or the ZCR533-CFA/I+mLT vaccine construct.
Figure 4:
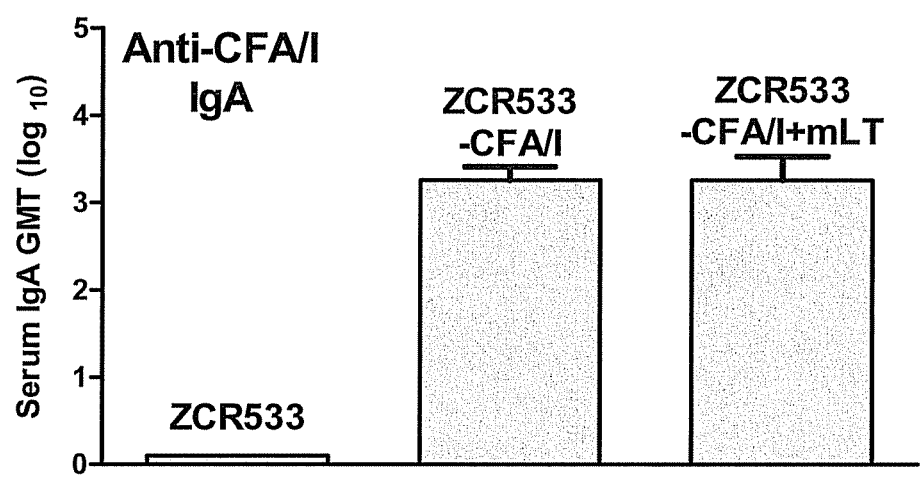
FIG. 4 shows serum α-CFA/I IgA response in mice vaccinated with ZCR533 EHEC vector, the ZCR533-CFA/I vaccine construct, or the ZCR533-CFA/I+mLT vaccine construct.
Figure 5:
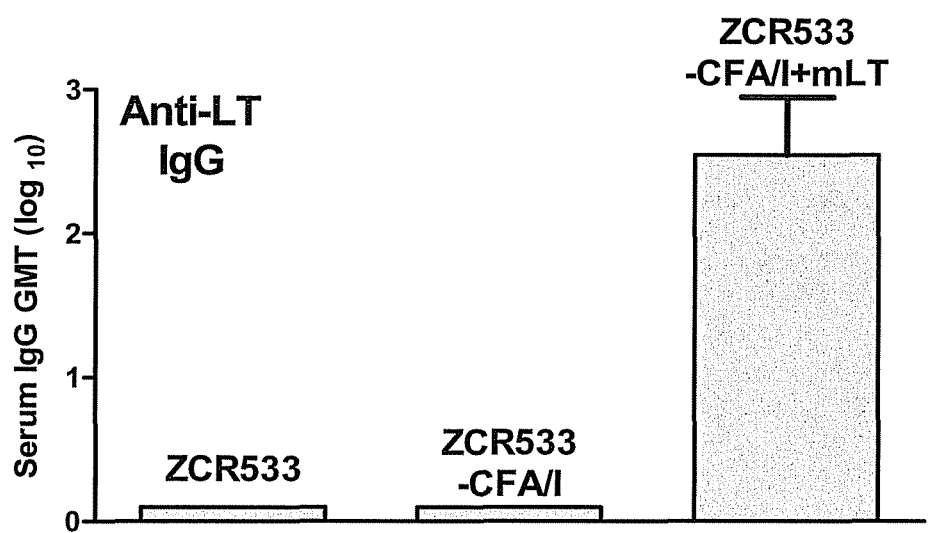
FIG. 5 shows serum α-LT IgG response in mice vaccinated with ZCR533 EHEC vector, the ZCR533-CFA/I vaccine construct, or the ZCR533-CFA/I+mLT vaccine construct.
Figure 6:
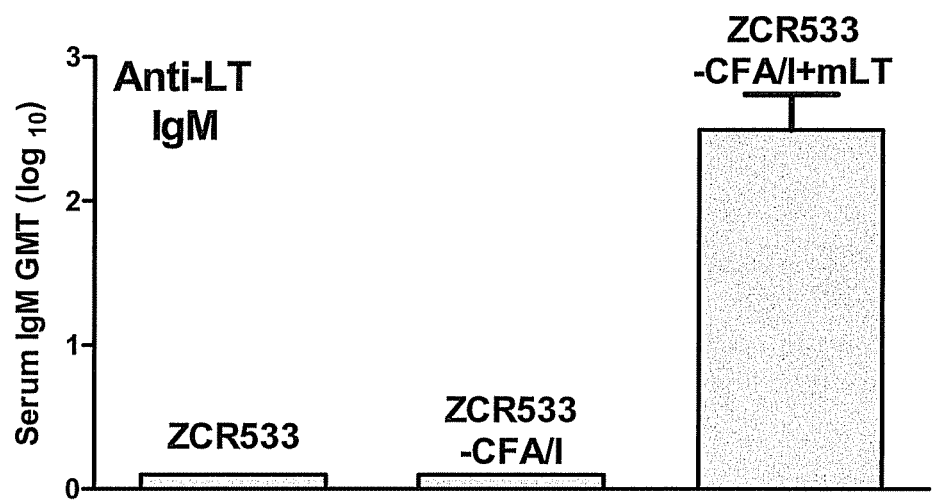
FIG. 6 shows serum α-LT IgM response in mice vaccinated with ZCR533 EHEC vector, the ZCR533-CFA/I vaccine construct, or the ZCR533-CFA/I+mLT vaccine construct.
Figure 7:
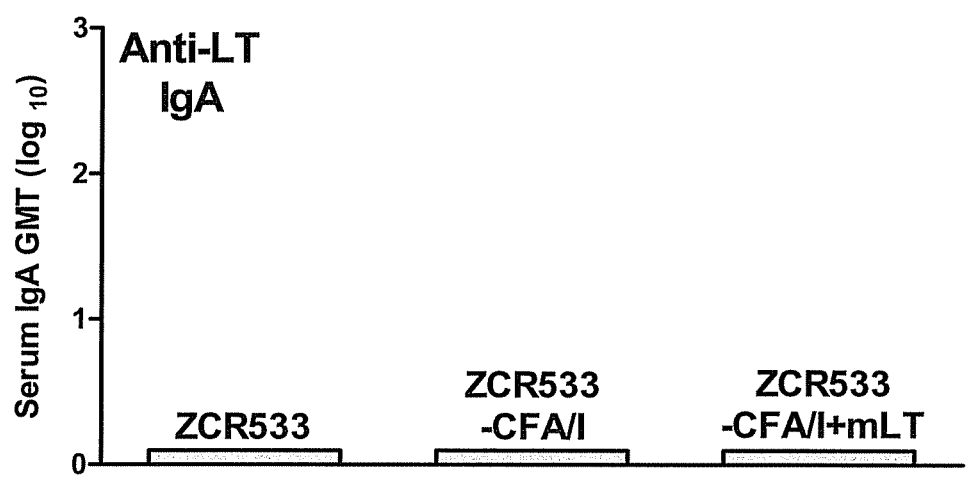
FIG. 7 shows serum α-LT IgA response in mice vaccinated with ZCR533 EHEC vector, the ZCR533-CFA/I vaccine construct, or the ZCR533-CFA/I+mLT vaccine construct.
Figure 8:
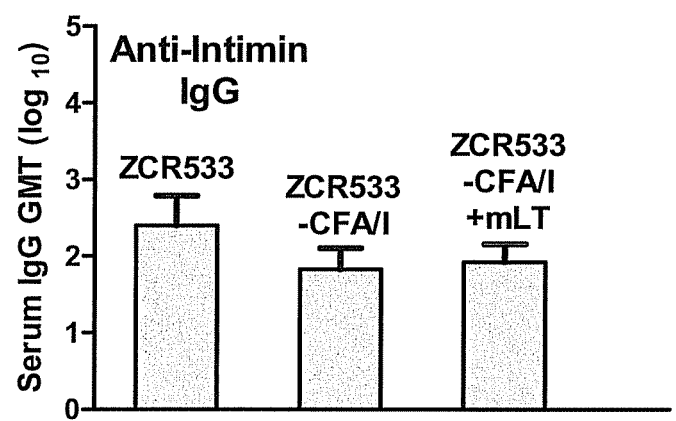
FIG. 8 shows serum α-Intimin IgG response in mice vaccinated with ZCR533 EHEC 7.5 vector, the ZCR533-CFA/I vaccine construct, or the ZCR533-CFA/I+mLT vaccine construct.
Figure 9:
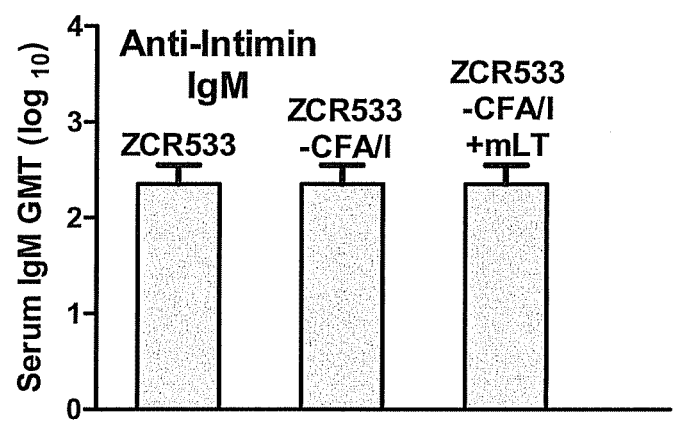
FIG. 9 shows serum α-Intimin IgM response in mice vaccinated with ZCR533 EHEC vector, the ZCR533-CFA/I vaccine construct, or the ZCR533-CFA/I+mLT vaccine construct.
Figure 10:
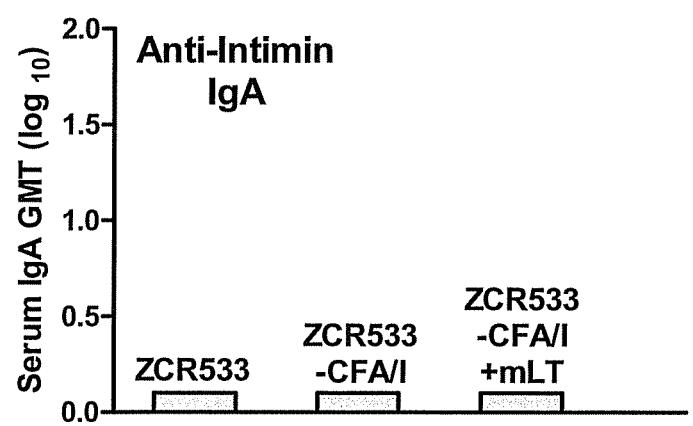
FIG. 10 shows serum Intimin IgA response in mice vaccinated with ZCR533 EHEC vector, the ZCR533-CFA/I vaccine construct, or the ZCR533-CFA/I+mLT vaccine construct.
Figure 11:
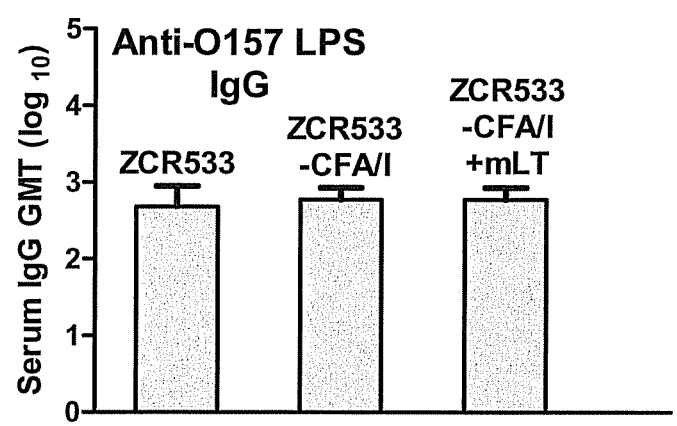
FIG. 11 shows serum α-O157 LPS IgG response in mice vaccinated with ZCR533 EHEC vector, the ZCR533-CFA/I vaccine construct, or the ZCR533-CFA/I+mLT vaccine construct.
Figure 12:
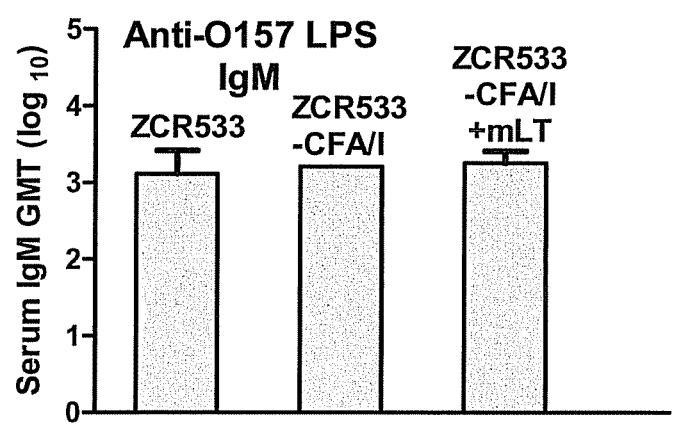
FIG. 12 shows serum α-O157 LPS IgM response in mice vaccinated with ZCR533 EHEC vector, the ZCR533-CFA/I vaccine construct, or the ZCR533-CFA/I+mLT vaccine construct.
Figure 13:
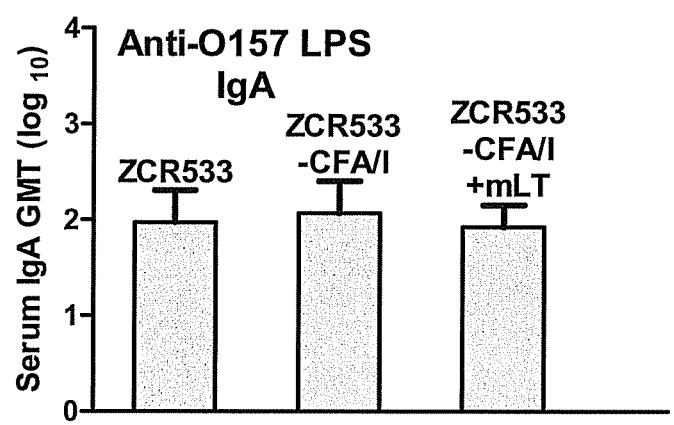
FIG. 13 shows serum α-O157 LPS IgA response in mice vaccinated with ZCR533 EHEC vector, the ZCR533-CFA/I vaccine construct, or the ZCR533-CFA/I+mLT vaccine construct.
Figure 14:
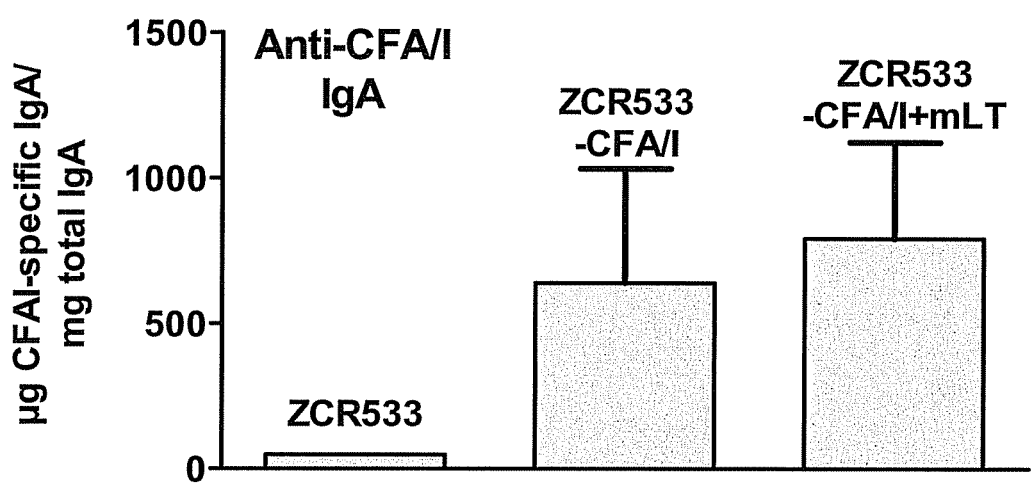
FIG. 14 shows nasal α-CFA/I IgA response in mice vaccinated with ZCR533 EHEC vector, the ZCR533-CFA/I vaccine construct, or the ZCR533-CFA/I+mLT vaccine construct.
Figure 15:
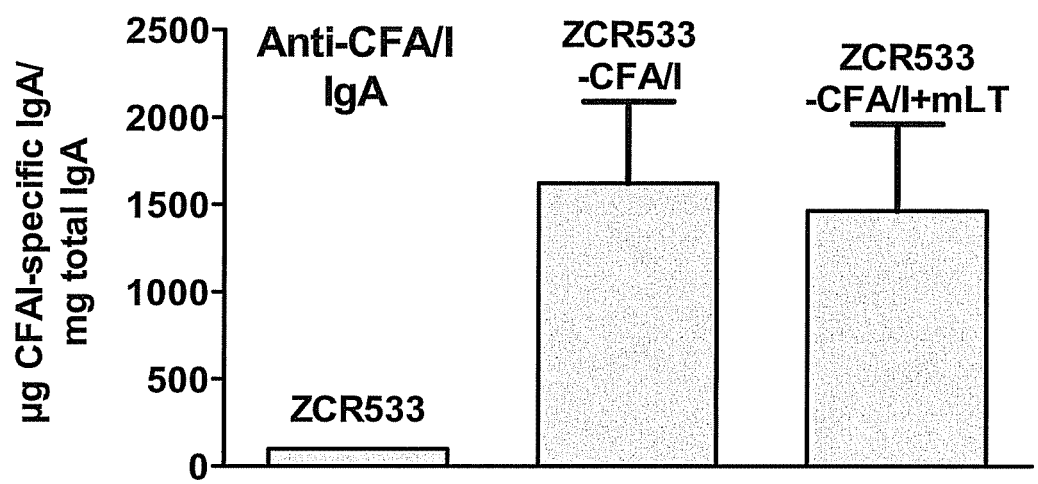
FIG. 15 shows lung α-CFA/I IgA response in mice vaccinated with ZCR533 EHEC vector, the ZCR533-CFA/I vaccine construct, or the ZCR533-CFA/I+mLT vaccine construct.
Figure 16:
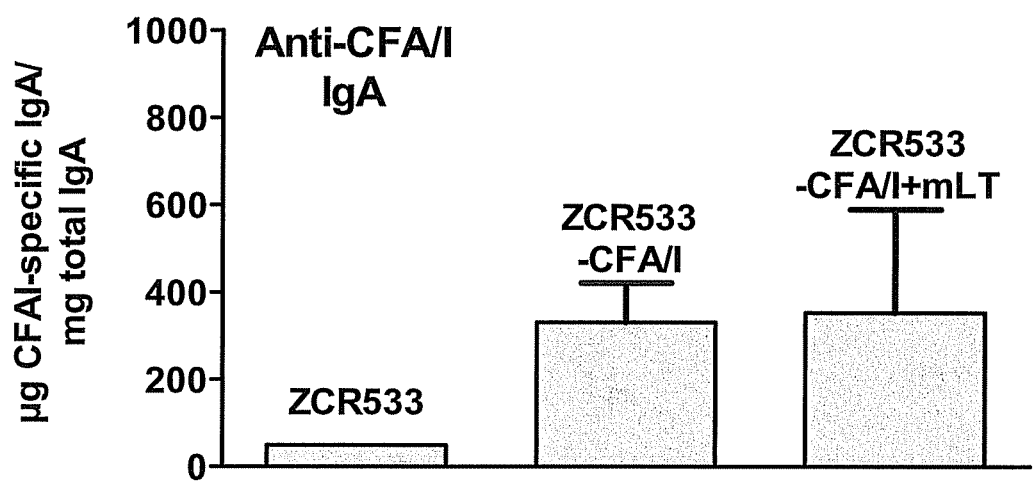
FIG. 16 shows small intestine α-CFA/I IgA response in mice vaccinated with ZCR533 EHEC vector, the ZCR533-CFA/I vaccine construct, or the ZCR533-CFA/I+mLT vaccine construct.
Figure 17:
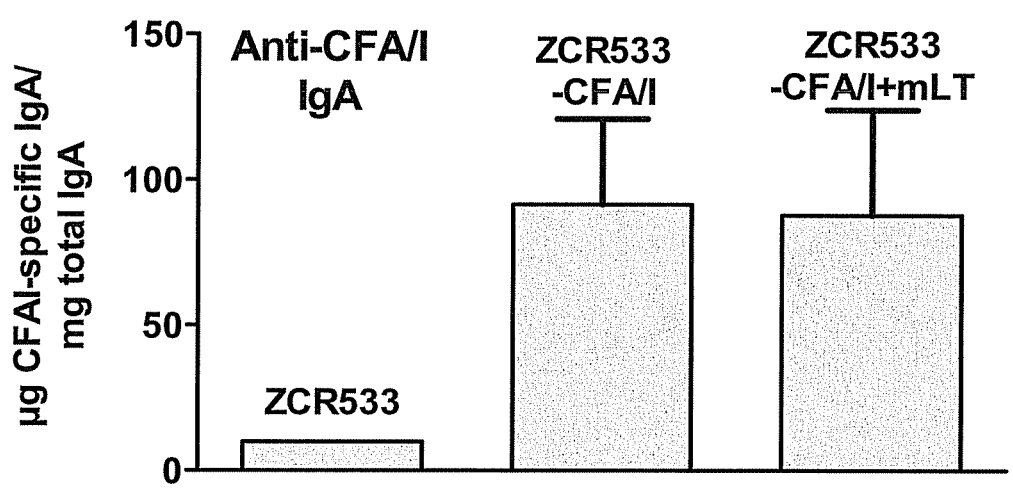
FIG. 17 shows fecal pellet α-CFA/I IgA response in mice vaccinated with ZCR533 EHEC vector, the ZCR533-CFA/I vaccine construct, or the ZCR533-CFA/I+mLT vaccine construct.
Figure 18:
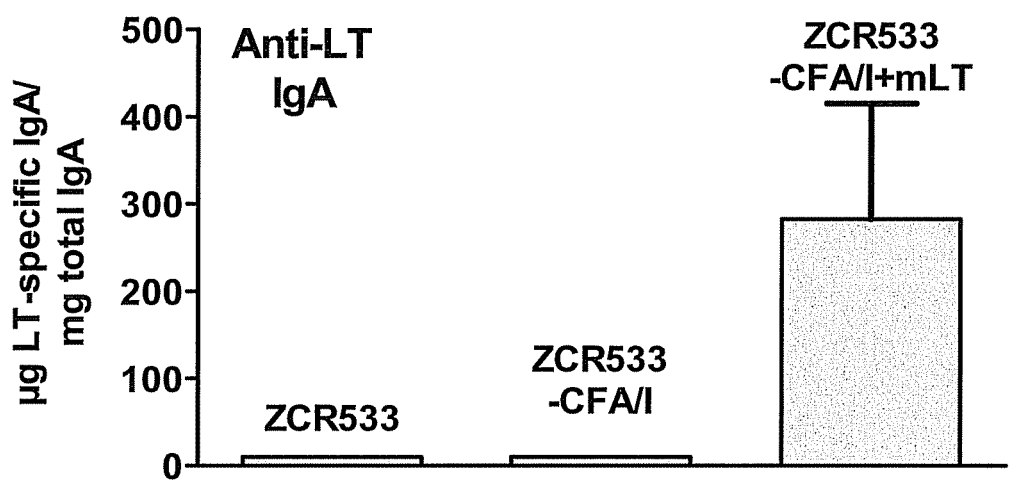
FIG. 18 shows nasal α-LT IgA response in mice vaccinated with ZCR533 EHEC vector, the ZCR533-CFA/I vaccine construct, or the ZCR533-CFA/I+mLT vaccine construct.
Figure 19:
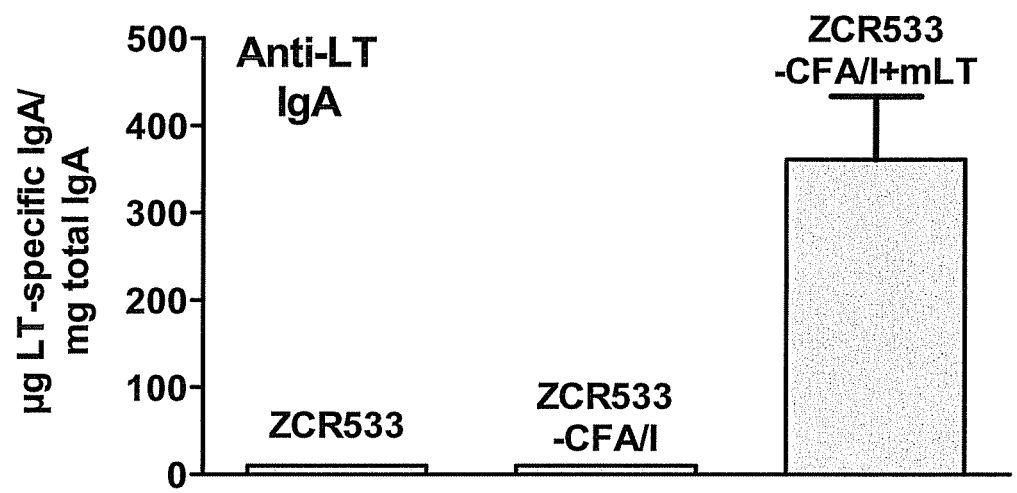
FIG. 19 shows lung α-LT IgA response in mice vaccinated with ZCR533 EHEC vector, the ZCR533-CFA/I vaccine construct, or the ZCR533-CFA/I+mLT vaccine construct.
Figure 20:
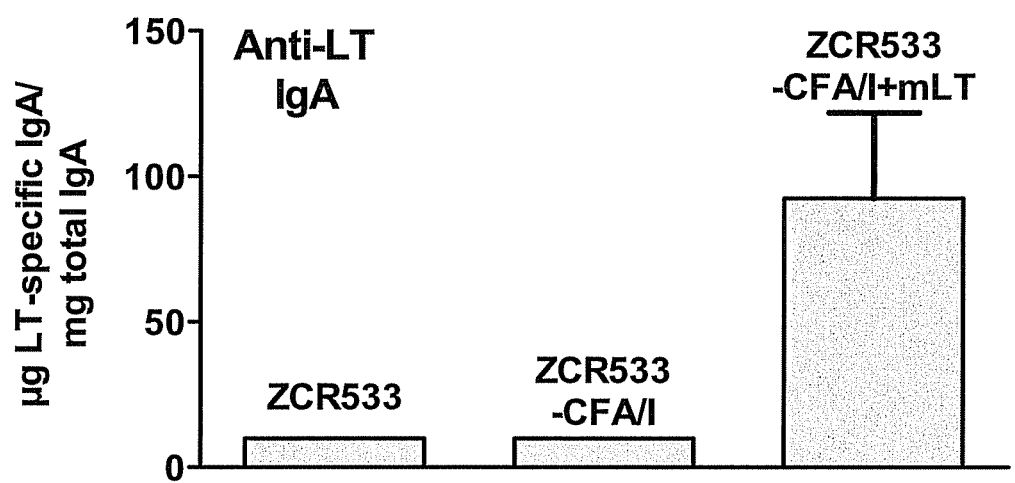
FIG. 20 shows small intestines α-LT IgA response in mice vaccinated with ZCR533 EHEC vector, the ZCR533-CFA/I vaccine construct, or the ZCR533-CFA/I+mLT vaccine construct.
Figure 21:
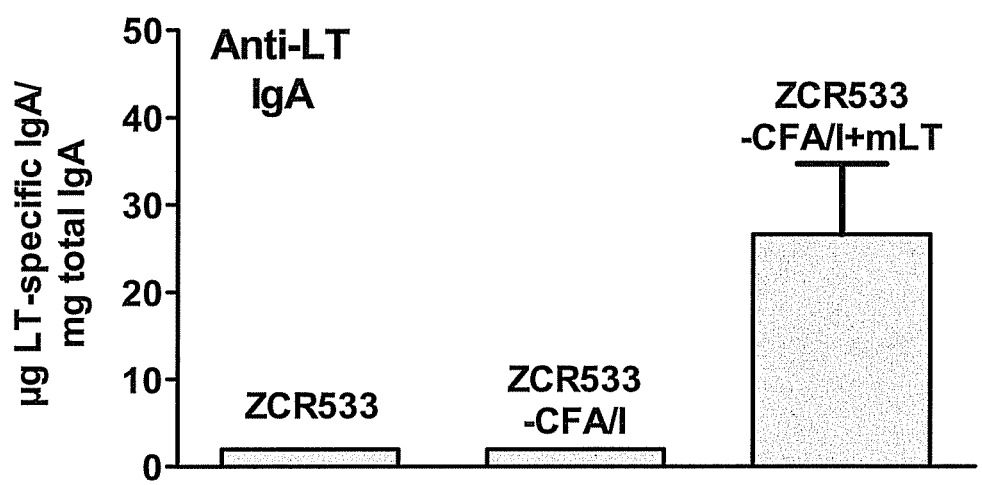
FIG. 21 shows fecal pellet α-LT IgA response in mice vaccinated with ZCR533 EHEC vector, the ZCR533-CFA/I vaccine construct, or the ZCR533-CFA/I+mLT vaccine construct.
Figure 22:
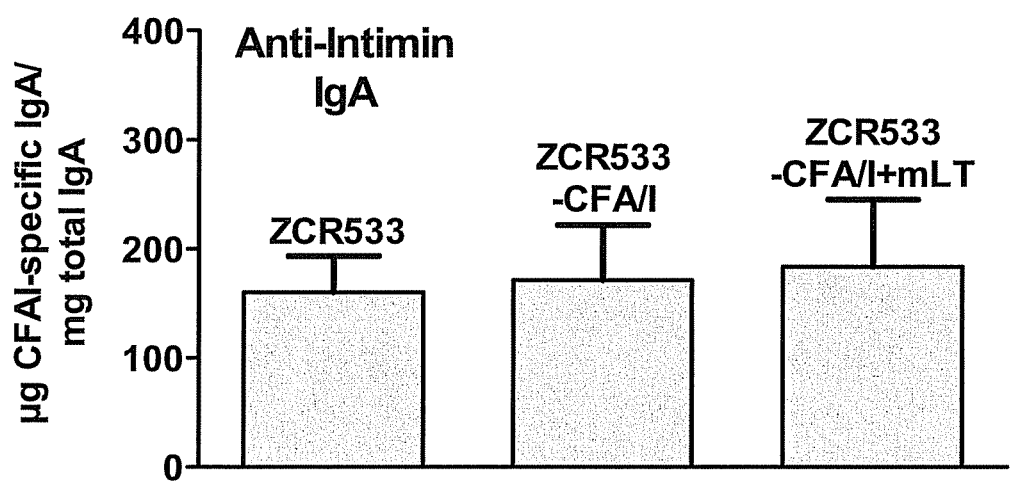
FIG. 22 shows nasal α-Intimin IgA response in mice vaccinated with ZCR533 EHEC 7.5 vector, the ZCR533-CFA/I vaccine construct, or the ZCR533-CFA/I+mLT vaccine construct.
Figure 23:
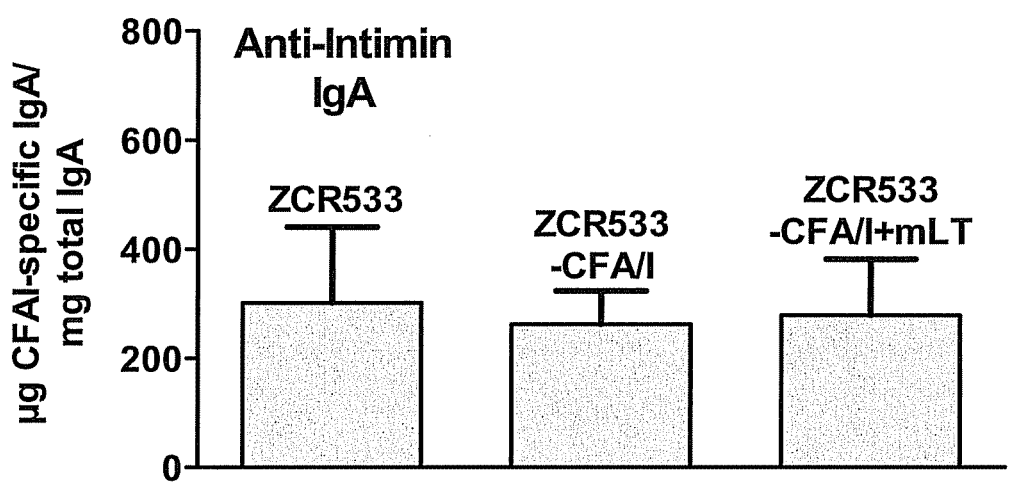
FIG. 23 shows lung α-Intimin IgA response in mice vaccinated with ZCR533 EHEC vector, the ZCR533-CFA/I vaccine construct, or the ZCR533-CFA/I+mLT vaccine construct.
Figure 24:
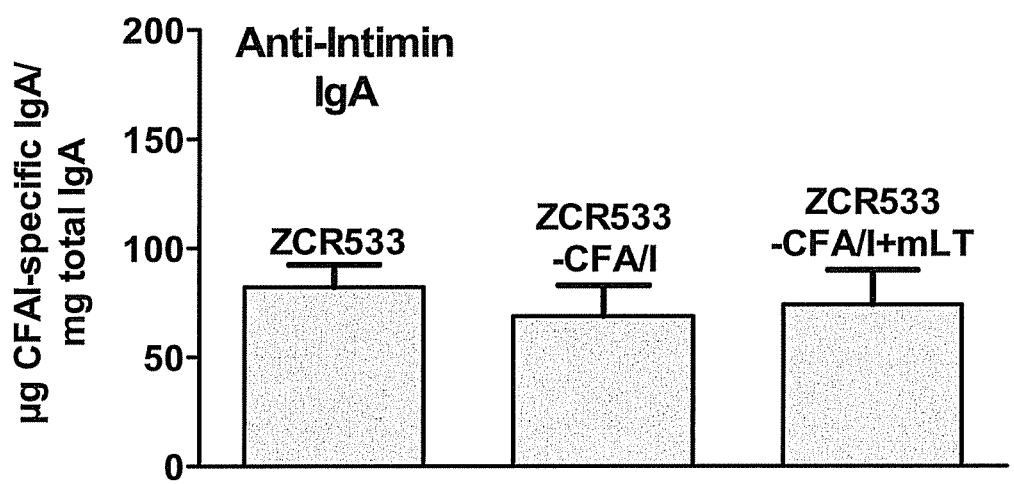
FIG. 24 shows small intestines α-Intimin IgA response in mice vaccinated with ZCR533 EHEC vector, the ZCR533-CFA/I vaccine construct, or the ZCR533-CFA/I+mLT vaccine construct.
Figure 25:
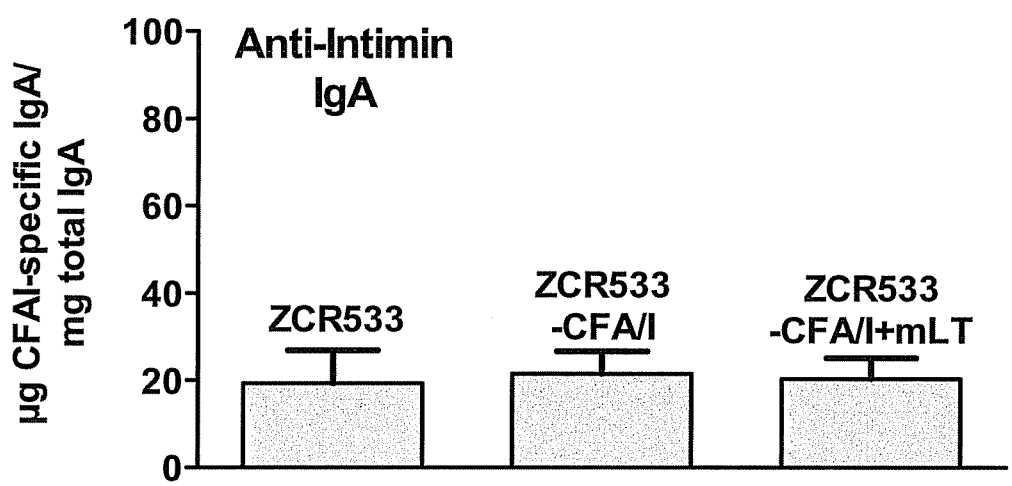
FIG. 25 shows fecal pellet α-Intimin IgA response in mice vaccinated with ZCR533 EHEC vector, the ZCR533-CFA/I vaccine construct, or the ZCR533-CFA/I+mLT vaccine construct.
Figure 26:
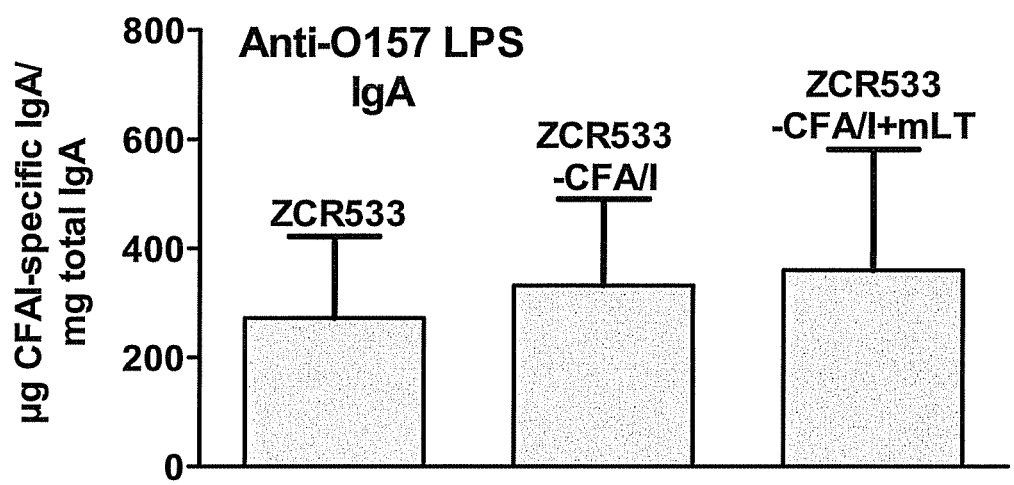
FIG. 26 shows nasal α-O157 LPS IgA response in mice vaccinated with ZCR533 EHEC vector, the ZCR533-CFA/I vaccine construct, or the ZCR533-CFA/I+mLT vaccine construct.
Figure 27:
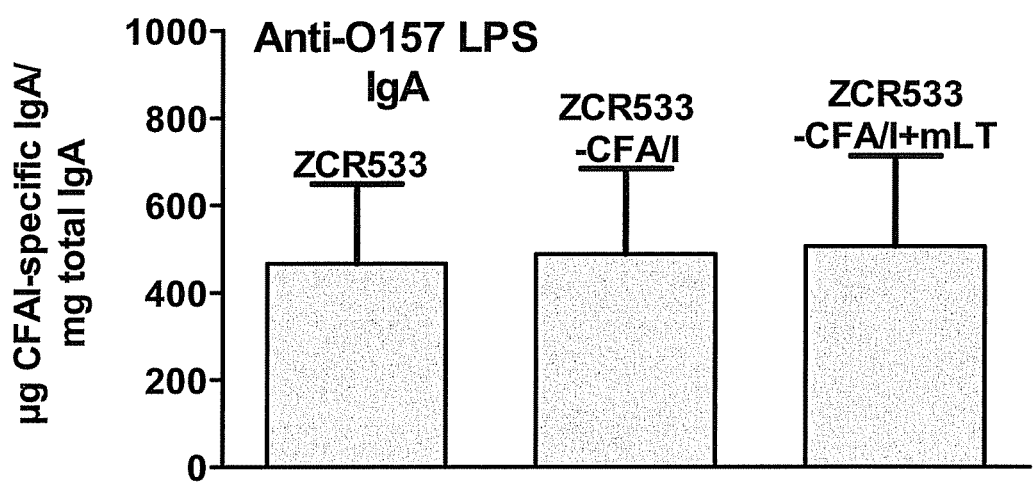
FIG. 27 shows lung α-O157 LPS IgA response in mice vaccinated with ZCR533 EHEC vector, the ZCR533-CFA/I vaccine construct, or the ZCR533-CFA/I+mLT vaccine construct.
Figure 28:
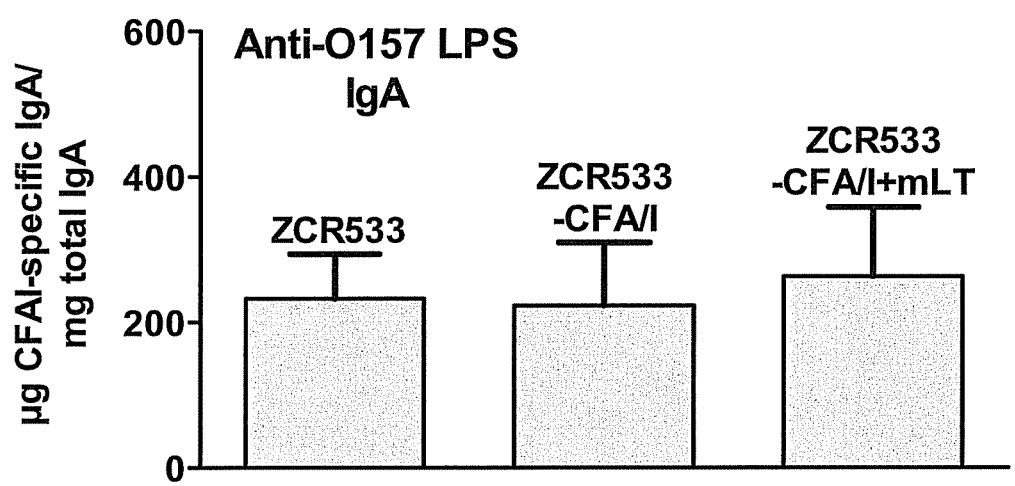
FIG. 28 shows small intestines α-O157 LPS IgA response in mice vaccinated with ZCR533 EHEC vector, the ZCR533-CFA/I vaccine construct, or the ZCR533-CFA/I+mLT vaccine construct.
Figure 29:
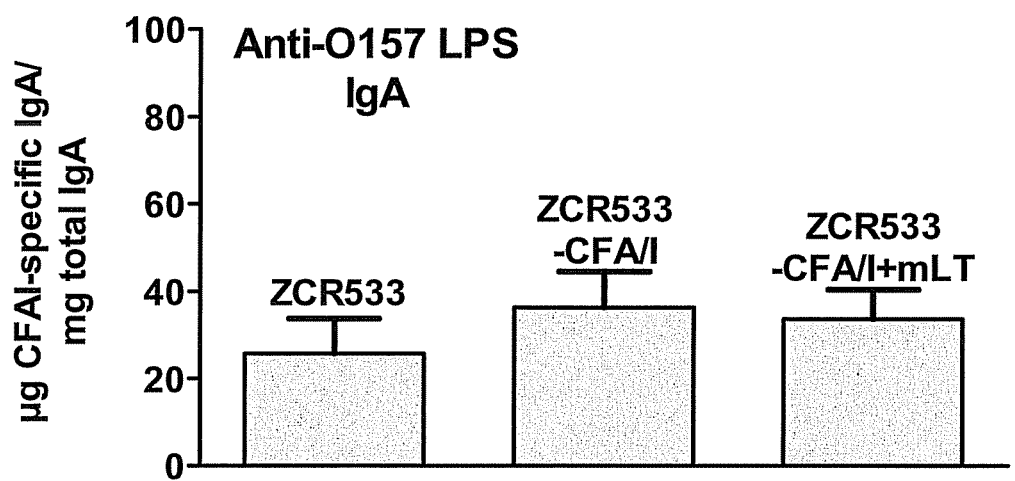
FIG. 29 shows fecal pellet α-O157 LPS IgA response in mice vaccinated with ZCR533 EHEC vector, the ZCR533-CFA/I vaccine construct, or the ZCR533-CFA/I+mLT vaccine construct.

We have developed live, attenuated vaccine vectors based on enterohemorrhagic *E. coli* (EHEC) strains. In some cases, the vector is modified to express one or more immunogens such as, for example, one or more protective enterotoxigenic *E. coli* antigens. As our vaccine vector, we use an attenuated attaching/effacing *E. coli* strain with minimal reactogenicity derived from an O157:H7 enterohemorrhagic *E. coli* isolate. We have prepared attenuated, live vaccine constructs by introducing plasmids containing cloned segments of DNA encoding representative immunogens into the attenuated EHEC vector. As representative immunogens, we have selected certain virulence determinants of enterotoxigenic *E. coli* (e.g., the colonization factor antigen I (CFA/I) and the heat-labile enterotoxin (LT)). To test the safety, immunogenicity, and protective efficacy of the constructs we use a novel mouse model of intranasal immunization and enterotoxigenic *E. coli* challenge. The attenuated, live vector, modified to express enterotoxigenic *E. coli* virulence determinants induces a protective immune response against a future lethal enterotoxigenic *E. coli* challenge. These studies have resulted in the development of a safe and effective live, attenuated vector. One use for such a vector is the construction and administration of a vector-based vaccine directed against enterotoxigenic *E. coli* infections.

The term "immunogen" and variants thereof refer to any material capable of inducing an immune response in a subject challenged with the material. An immunogen may occur naturally or reflect a truncated, chimeric, or otherwise modified version of a naturally occurring immunogen. Thus, an immunogen may represent a full length protein or polypeptide as naturally expressed or may represent an immunogenic portion or may reflect a modified version of such a polypeptide having at least one addition, deletion, or substitution.

The term "protect" and variants thereof refers to any decrease in the likelihood and/or extent of infection and/or pathology due to infection, including, for example, any amelioration and/or decrease in the occurrence and/or severity of clinical signs or symptoms of a condition caused by infection by the pathogen.

The term "sign" or "clinical sign" refers to an objective physical finding relating to a particular condition capable of being found by one other than the patient.

The term "symptom" refers to any subjective evidence of disease or of a patient's condition.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Enterotoxigenic *E. coli* are noninvasive and colonize the small intestine by attachment to mucosal receptors via surface-expressed hair-like fimbrial colonization factor adhesins (e.g., CFA/I, CS1, CS2, CS4, CS5) or finer fibrillar colonization factor adhesins (e.g., CS3, CS6) made of repeating structural subunits. The binding of enterotoxigenic *E. coli* to specific glycoprotein receptors or glycolipid receptors present on the mucosa is mediated by a subset of adhesive subunits that may be expressed at the tips of fimbriae. Intact fimbriae, or their structural or adhesive subunits, are appropriate targets for inclusion in vaccines in order to induce mucosal antibodies that will prevent small bowel colonization. Certain colonization factor antigens associated with enterotoxigenic *E. coli* strains have been grouped into families that may share immune determinants. Three colonization factors (CFA/I, CS3, and CS6) are expressed by the majority of enterotoxigenic *E. coli* isolates.

Enterotoxigenic *E. coli* that adhere to the mucosa of the small intestine produce heat-labile (LT) and/or heat-stable (ST) enterotoxins. Expression of these toxins can result in a watery, non-inflammatory diarrheal disease in the host. The primary cause of morbidity and mortality is dehydration.

Heat-labile toxin (LT) is a typical A1B5 toxin whose pentameric B subunit binds to its GM1 ganglioside host receptor, allowing the A subunit to activate adenylate cyclase resulting in increased cyclic AMP and enhanced chloride secretion. LT components are appropriate for inclusion in vaccines to target bacterial strains that express only LT as well as strains that express both LT and heat-stabile (ST) enterotoxins. The B subunit of LT is an effective immunogen and protective antigen, whereas the holotoxin has important immune adjuvant properties. Mutants of the holotoxin have been developed which have lost secretory activity but maintain adjuvant activity.

Heat-stable toxin (ST) is a small molecule that binds guanylate cyclase thereby increasing cyclic GMP, net chloride secretion, and, therefore, watery diarrhea. ST may not induce immunity in natural infection. Since ST has not been shown to be a reliable, practical vaccine target, immunity to strains that express ST but not LT typically exploit the immunogenicity of other antigens such as, for example, adhesins.

More than one hundred serotypes associated with enterotoxigenic *E. coli* based on lipopolysaccharide (O) and flagellar (H) typing have been identified. Common serotypes account for only about 15% of the enterotoxigenic *E. coli* in individual studies. Therefore, lipopolysaccharide and/or flagellar antigens are less suitable targets for designing broad spectrum enterotoxigenic *E. coli* vaccines.

At present, there is no licensed enterotoxigenic *E. coli* vaccine. Enterotoxigenic *E. coli* vaccine development is geared towards inducing mucosal immune responses to (a) block initial colonization of enterotoxigenic *E. coli* in the gut and (b) neutralize enterotoxigenic *E. coli* toxins. Epidemiological studies, as well as volunteer trials and animal studies, have shown that acquired immunity to enterotoxigenic *E. coli* infection is mainly a result of anti-colonization factor immune responses. Thus, mucosal antibodies against CFAs can induce a protective response against enterotoxigenic *E. coli* infections. Such protection does not necessarily depend upon bactericidal immune activity. Rather, the protection may result from intestinal secretory IgA antibodies directed against enterotoxigenic *E. coli* colonization factors to prevent small bowel colonization.

One candidate for a human enterotoxigenic *E. coli* vaccine is a mixture of killed wild-type enterotoxigenic *E. coli* strains chosen for their expression of the most common CFAs, supplemented with the recombinant B subunit of cholera toxin (chosen as a homolog of the B subunit of LT). It has shown modest efficacy in protecting travelers from diarrheal episodes, but, although immunogenic, it showed no efficacy against vaccine preventable events in a large field trial in Egyptian children.

Another candidate for a human enterotoxigenic *E. coli* vaccine includes enterotoxigenic *E. coli* CFAs encapsulated in biodegradable, biocompatible poly-lactide-co-glycolide (PLGA) microspheres. The microspheres are designed to target M cell uptake with slow release of the antigens in mucosal inductive sites. Microsphere vaccines have been tested in human volunteer challenge studies and in an intranasal mouse challenge model. These microsphere vaccines have not been demonstrated to induce consistent immune responses.

A spontaneously derived nontoxigenic LT- and ST-ETEC strain expressing the CS1 and CS3 components of CFA/II can induce serum and/or intestinal antibody responses to CFA/II components in volunteers vaccinated with the strain. Moreover, 75% of the volunteers were protected against challenge with a wild-type CFA/II ETEC strain of different serotype. Thus, protection against ETEC challenge can be induced by immunity to CFAs. However, this ETEC strain caused some vaccines to develop cramps and diarrhea. Subsequently, this strain has been further attenuated by chromosomal deletion of genes for utilization of aromatic amino acids (aroC) and for outer membrane proteins (e.g., ompR (PTL002) or ompC and ompF (PTL003)), which were better tolerated. Despite being well tolerated, development and testing of these attenuated vaccines has been suspended.

Pathogenic but noninvasive E. coli such as, for example, attaching/effacing E. coli (AEEC) have strong potential as vectors for oral vaccines. Advantages of using AEEC strains for expressing ETEC antigens include, for example, maintenance of their native configuration and the targeting of Peyer's patches. We have attenuated attaching/effacing E. coli strains by modifying virulence genes encoded on the locus of enterocyte effacement (LEE) pathogenicity island (PAI) and have shown these constructs to be safe and effective vaccines. We now describe using such strains as vectors to deliver ETEC antigens.

The genes sufficient for the development of Attaching/Effacing (A/E) adherence by enteropathogenic (EPEC) and enterohemorrhagic (EHEC) E. coli are contained in a pathogenicity island termed the locus of enterocyte effacement (LEE). To develop attenuated A/E strains as vaccines and vectors in animal models of intestinal disease we utilized rabbit enteropathogenic E. coli (REPEC) strains. The LEE of REPEC strain RDEC-1 (O15:H—) was sequenced and found to be highly homologous to the LEEs of EPEC and EHEC. All three LEEs contain a shared core region of 40 open reading frames. Among the shared genes, high homology (>95% identity) between the RDEC-1 and the EPEC and EHEC LEEs at the predicted amino acid level was observed for the components of the type III secretion apparatus, and the Ler (LEE-encoded regulator). More divergence (66% to 88% identity) was observed in genes encoding proteins involved in host interaction, such as the adhesin intimin (Eae) and the secreted protein Tir (translocated intimin receptor). We used this sequence information to attenuate REPEC strains by creating in-frame deletion mutants or gene truncations in key virulence genes of the LEE. We then tested these mutants for attenuation, for immunogenicity, and for protective efficacy against challenge with virulent A/E pathogens.

We have developed a vaccine vector relevant to human disease based on an eae truncation mutant of an O157:H7 shiga toxin producing E. coli (STEC) strain that had been negative for shiga toxin 1 and was deleted for shiga toxin 2. The resulting vector strain is designated herein as ZCR533. While ZCR533 has been developed for use as a vaccine vector in cattle, O157 EHEC are non-pathogenic in cattle. (U.S. Patent Application Publication No. 2008/0286310 A1). In contrast, O157 EHEC are pathogenic in, for example, mice and humans. Thus, it was unclear whether attenuation of the vector would necessarily result is a vector-based vaccine that would be well tolerated in, for example, mice and humans. Here we show that in mice, the O157:H7 Stx1-, Stx2-, Δ-eae strain ZCR533 did not produce A/E lesions in vitro, but induced mucosal and serum antibody to intimin. Thus, the strain can serve as a vaccine for human subjects against O157 EHEC infection.

Construction of the ZCR533 vector is described in U.S. Patent Application Publication No. 2008/0286310 A1. The vector may be a component of a vaccine useful for delivering to a subject one or more immunogens whose coding sequence is cloned into and expressed by the vector. Coding sequences for immunogens may be cloned into the vector using standard techniques well-known to those skilled in the art.

Any suitable immunogen may be delivered to a subject in this way. Suitable immunogens include, for example, immunogens naturally expressed by enterotoxigenic E. coli such as, for example, heat stabile enterotoxin (ST), heat-labile enterotoxin (LT), colonization factor antigen I (CFA/I), intimin, and lipopolysaccharide (LPS) such as, for example, LPS naturally expressed by O157 E. coli.

In other cases, however, the vector may be useful more generally to deliver an immunogen to a subject that is naturally expressed by other microbes. Thus, exemplary immunogens can include immunogens naturally expressed—or derived from immunogens naturally expressed—by, for example, Gram-negative microbes, Gram-positive microbes, fungi, viruses, and the like.

Thus an immunogen may be expressed by or derived from a protein or polypeptide expressed by—a Gram-negative microbe. Suitable Gram-negative microbes from which an immunogen may be expressed or derives can include, for example, an enteropathogen such as, for example, a member of the family Enterobacteriaceae. Exemplary enteropathogens include members of the family Enterobacteriaceae, members of the family Vibrionaceae (including, for instance, Vibrio cholerae), and Campylobacter spp. (including, for instance, C. jejuni). Exemplary members of the family Enterobacteriaceae include, for instance, E. coli, Shigella spp., Salmonella spp., Proteus spp., Klebsiella spp. (for instance, Klebsiella pneumoniae), Serratia spp., and Yersinia spp. Exemplary Salmonella spp. include, for example, Salmonella enterica serovars, Bredeney, Dublin, Agona, Blockley, Enteriditis, Typhimurium, Hadar, Heidelberg, Montevideo, Muenster, Newport senftenberg, Salmonella cholerasuis, and S. typhi. Exemplary strains of E. coli include, for example, E. coli serotypes O1a, O2a, O78, and O157, different O:H serotypes including 0104, 0111, 026, 0113, 091, and hemolytic strains of enterotoxigenic E. coli such as K88$^+$, F4$^+$, F18ab$^+$, and F18ac$^+$. Other exemplary Gram-negative microbes include members of the family Pasteurellaceae (e.g., Pasturella spp. such as, for example, Pasteurella multocida and Pasteurella haemolytica) and members of the family Pseudomonadaceae (e.g., Pseudomonas spp. such as, for example, Pseudomonas aeruginosa). Yet other exemplary Gram-negative microbes include, for example, Actinobacillus spp., Haemophilus spp., Myxcobacteria spp., Sporocytophaga spp., Chondrococcus spp., Cytophaga spp., Flexibacter spp., Flavobacterium spp., Aeromonas spp., and the like.

In other embodiments, an immunogen may be expressed by—or derived from a protein or polypeptide expressed by—a Gram-positive microbe. Suitable Gram-positive microbes from which an immunogen may be expressed or derived include, for example, members of the family Micrococcaceae such as, for example, Staphylococcus spp. (e.g., Staphylococcus aureus). Other Gram-positive microbes include members of the family Deinococcaceae, (e.g., Streptococcus agalactiae, Streptococcus uberis, Streptococcus bovis, Streptococcus equi, Streptococcus zooepidemicus, or Streptococcus dysgalatiae), Bacillus spp., Corynebacterium spp., Erysipelothrix spp., Listeria spp., and Mycobacterium spp., Erysipelothrix spp., and Clostridium spp.

In other embodiments, an immunogen may be expressed by or derived from a protein or polypeptide expressed by a fungus. Suitable fungi from which an immunogen may be expressed or derived include, for example, *Cryptococcus* spp., *Blastomyces* spp. (e.g., *B. deratitidis*), *Histoplasma* spp. *Coccidiodes* spp., *Candida* spp. (e.g., *C. albicans*), and *Aspergillus* spp.

In other embodiments, an immunogen may be—or be derived from—a viral protein or polypeptide. Suitable viruses from which an immunogen may be identified or derived include, for example DNA viruses and RNA viruses such as, for example, picornaviruses (e.g., enteroviruses, rhinoviruses, aphthoviruses, and hepatoviruses), coronaviruses, flaviviruses, hepaciviruses, morbilliviruses, metapneumoviruses, rubulaviruses, and lentiviruses.

In another aspect, the present invention provides a vector that can induce an immune response against both one or more native EHEC immunogens and one or more heterologous immunogens cloned into and expressed by the vector. In this aspect, the invention provides a tool by which vaccination against multiple pathogens (e.g., EHEC and ETEC, EHEC and *Brucella* spp.) can be achieved. It is not a given that immunogenicity and/or protection versus EHEC challenge can be maintained when the vector expresses one or more heterologous immunogens because it is possible, for example, that expression of one or more heterologous immunogens can interfere with and/or overwhelm an immune response against EHEC immunogens. Table 3 shows that mucosal antibody responses to exemplary EHEC immunogens intimin and O157 LPS were maintained when the vector was modified to express ETEC immunogens.

As used herein a subject can be an animal such as, for example, humans, dogs, cats, cattle, horses, sheep, swine, rodents, and the like. In some cases, the subject animal can be livestock (e.g., cattle, horses, swine, etc.) or a companion animal (e.g., dogs, cats, etc.). In some cases, the subject animal is an animal in which wild-type EHEC is a pathogen.

In another aspect, the invention includes a small animal model for the study of immunogenicity and efficacy of the vaccines described herein following ETEC challenge.

Lack of a small animal model has hampered the study of pathogenesis and immunogenicity of ETEC infection. Some studies involving ETEC have utilized the suckling mouse for ST effects, rats, guinea pigs, or rabbits for LT effects. However, the species-specificity of ETEC adhesins for receptors present in human intestine has prevented the establishment of an animal model for small bowel adherence and colonization with human isolates. Transient obstruction of the small intestine with a removable intestinal tie in an adult rabbit diarrhea model (RITARD) has permitted small bowel colonization to occur without adherence, but this procedure is surgically invasive and does not permit the study of the contribution of CFAs to pathogenesis.

Intranasal challenge models using mice for the study of the immunopathogenesis of an enteric infection with *Shigella*, another host-restricted pathogen, have exploited the mouse lung as a simplified model for the study of the pathogenesis and immunobiology of *Shigella* infection. The mucosal surface of the bronchus of the mouse shares some characteristics with the intestinal epithelium mucosal surface, although the tracheobronchi of the mouse have ciliated columnar epithelium and the alveolar sacs cuboidal epithelium. The bronchial wall contains lymphoid follicles that are similar to mouse intestinal Peyer's patches and the lungs having antigen-presenting cells as well as B lymphocytes and T helper/suppressor lymphocytes. In addition, systemic and local immune responses can be accurately evaluated after intranasal challenge since the mouse lung is immunologically naive with respect to specific antigens. Moreover, the absence of commensal bacteria in the bronchial lumen means that the lung has not been primed by previous exposure to other Gram-negative bacteria. The intranasal administration of both *Shigella* spp. and *Campylobacter jejuni* to mice has been used to study vaccine candidates, pathogenesis, and vaccination-acquired immunity.

The utility of an intranasal challenge model is supported by the acceptance of the intranasal route as an effective means of stimulating mucosal immunity, which is sparing of antigen and which results in increased IgA responses at mucosal surfaces within the common mucosal immune system. This is the desired type of immunity to protect against non-invasive pathogens, like ETEC, which colonize mucosal surfaces. Furthermore, protection can be achieved at distant mucosal sites (such as the intestine) via intranasal vaccination. Moreover, intranasal immunization can also induce systemic immune responses. Nasal-associated lymphoid tissue (HALT) of intranasally immunized mice, but not of naïve mice, contains antigen-specific IgA antibody secreting cells (ASC), indicating that B-cell activation and IgA isotype switching occurs in NALT. NALT serves as an inductive site for antigen-specific IgA ASC that migrate to distant mucosal effector sites following intranasal immunization. Furthermore, memory T cells reside in NALT for extended periods. The presence of NALT in the upper respiratory tract and the ability to disseminate antigen-specific IgA ASC to distant mucosal effector sites support use of intranasal immunization.

We describe herein an intranasal challenge model using the ETEC strains H10407 and B7A, and use this model to effectively study the immunogenicity and efficacy of CFA and toxin-based vaccines. Although physiologic conditions present in the GI tract, but absent in the respiratory tract (including acidic pH, proteolytic enzymes, bile salts, peristalsis, the microbiota, and usual target cells for bacterial and toxin binding), may affect the course of an ETEC infection and the expression of ETEC antigens, the intranasal mouse model can nevertheless permit the valid study of anti-CFA and anti-toxin immunity following immunization and challenge. Thus, the intranasal route of inoculation can be used effectively both for mucosal immunization with ETEC antigens and to produce a reproducible model of ETEC infection resulting in multifocal bronchopneumonia with no evidence of systemic spread outside the lungs.

Vaccine candidates containing plasmids expressing either CFA/I, alone, or CFA/I plus mutant *E. coli* LT express CFA/I fimbriae on their surface. CFA/I fimbriae manifest both hemagglutinating and hydrophobic properties characteristic of the wild-type fimbriae. In addition, the vaccine with the mLT encoding plasmids expressed LT in its periplasmic space. Both of the expression plasmids tested proved to be stable in 70% of bacteria after 100 generations in vitro and were stable in vivo for 10 days after intranasal administration. A summary of the properties of the vectors is provided in FIG. 1

To establish that our ZCR533 EHEC vector and its related vaccine strains can be safely administered intranasally to mice at doses which are immunogenic, we administered a range of doses (from $1\times10^7$ to $5\times10^9$) of the ZCR533 EHEC vector and of the EHEC(CFA/I) and EHEC (CFA/I-mLT) vaccines strains intranasally to mice in a volume of 20 μl.

Safety was determined by clinical observation of signs of distress. Doses of up $5\times10^7$ bacteria of the vaccine vector (or its derivative expressing CFA/I and mLT) administered intranasally in a 20 μl volume caused no distress in any animals. Animals receiving up to $1\times10^9$ showed only mild and transient distress.

Immunogenicity for a single dose (or two doses) was assessed by: (a) the ability of sera obtained at 14 days after the final dose to agglutinate a suspension of the vector ZCR533 and the wild-type (WT) H10407, and (b) ELISAs against whole cells of the EHEC ZCR533 vector and of WT H10407 expressing CFA/I. Results are shown in Table 1.

TABLE 1

Serum Antibody Responses Induced by Intranasal Immunizations

|  | Serum against ZCR533 EHEC Vector Strain | Serum against ETEC H10407 WT Strain | Serum against ZCR533 (CFA/I-mLT) Vaccine Strain |
|---|---|---|---|
| Slide Bacterial agglutination of ZCR533 vector | Positive 2 doses ($5 \times 10^7$ CFU) | Negative | Positive 2 doses ($5 \times 10^7$ CFU) |
| Slide Bacterial Agglutination of WT H10407 | Negative ($1 \times 10^7$ to $5 \times 10^9$ CFU) | Positive ($1 \times 10^7$ to $1 \times 10^9$ CFU) | Positive ($1 \times 10^7$ to $5 \times 10^9$ CFU) |
| Serum ELISA IgG titers against ZCR533 vector | +1/60 at ($5 \times 10^7$ CFU) +1/180 at ($1 \times 10^8$ CFU) | Negative ($1 \times 10^7$ to $5 \times 10^9$ CFU) | +1/60 at ($1 \times 10^8$ CFU) +1/180 at ($5 \times 10^8$ CFU) |
| Serum ELISA IgG titers against whole cell H10407 | Negative ($1 \times 10^7$ to $5 \times 10^9$ CFU) | +1/180 at ($1 \times 10^7$ CFU) +1/540 at ($1 \times 10^9$ CFU) | +1/180 at ($1 \times 10^7$ CFU) +1/540 at ($5 \times 10^8$ CFU) +1/1620 at ($5 \times 10^9$ CFU) |

These results indicate that an immune response against the vector can be induced by two immunizations with a safe dose ($5 \times 10^7$ CFU) of the vaccine vector itself. Similar safe single doses of the ZCR533 (CFA/I-mLT) vaccine strain induced slide agglutination of the WT CFA/I+H10407 as well as measurable ELISA titers to these organisms. The ELISA titers and agglutinating activity induced by the vaccine was comparable to those induced by intranasal administration of the WT H10407 at sub lethal doses.

The present invention is illustrated by the following examples. It is to be understood that the particular examples, materials, amounts, and procedures are to be interpreted broadly in accordance with the scope and spirit of the invention as set forth herein.

EXAMPLES

Example 1

Female BALB/c mice (6-8 weeks of age) were anesthetized with isoflurane and a range of doses ($1 \times 10^7$-$1 \times 10^8$ CFUs) of the vaccine construct (ZCR533-CFA/I and ZCR533-CFA/I plus mLT) administered in a 20 µl volume drop-wise to the external nares of each mouse. Following intranasal delivery of the vaccine constructs, the mice were observed for adverse effects for at least 14 days following administration of the vaccine constructs. The mice were monitored for adverse effects including ruffled fur, huddling, lethargy, shivering, labored breathing, difficulty in moving, refusal to eat or drink, drainage from eyes, hunched posture and/or moribund condition. Results are shown in Table 2.

TABLE 2

Effect of vector and vaccine constructs on BALB/c mice following intranasal delivery

| Strain | $1 \times 10^7$ CFU | $5 \times 10^7$ CFU | $1 \times 10^8$ CFU |
|---|---|---|---|
| ZCR533 | N | N | N |
| ZCR533-CFA/I | N | N | N |
| ZCR533-CFA/I + mLT | N | N | N |

N = No significant signs of distress in the mice

Example 2

Mice were administered intranasally two doses of the vaccine constructs ($5 \times 10^7$ bacteria per dose) in a 20 µl volume with an interval of 14 days. Fourteen days following the second dose of vaccine constructs, blood and mucosal collections (fecal pellets, nasal and lung lavages, and small and large intestinal washes) were obtained. Blood was collected from the mice by tail nick with a razor blade, clotted overnight at 4° C., centrifuged at 10,000×g for 10 minutes and the sera stored at −80° C. Fecal pellets were obtained by placing mice on absorbent paper under a 600-ml beaker for 10-15 minutes. Fecal pellets were placed in microfuge tubes with 1 ml of Protease Inhibitor Cocktail (PIC) (Sigma Chemical Co. St. Louis, Mo.), broken up with sterile toothpicks, centrifuged at 10,000×g for 15 minutes and supernatants stored at −80° C.

Lung lavages, nasal lavages, and small intestinal washes, and large intestinal washes were collected from the mice following euthanasia using carbon dioxide. For lung lavages, a catheter was inserted into the trachea and 1 ml of PIC used to inflate the lungs. For nasal lavages, a catheter was inserted into the trachea and 500 µl of PIC used to flush the nasal area with the fluid being collected from the nares. For small intestinal washes, the small intestines were cut about 1-2 cm from the stomach and about 1-2 cm from the cecum, and 2 ml of PIC flushed through the small intestines. For large intestinal washes, the large intestines were cut at the cecum and at the anus, and 500 µl of PIC flushed through the large intestines. All washes and lavages were centrifuged at 10,000×g for 15 minutes and the supernatants stored at −80° C.

Serum (IgG, IgA, and IgM) and mucosal (IgA and IgG) antibodies against CFA/I, LT, intimin and O157 LPS were measured by the use of an ELISA (Byrd, W. and F. J. Cassels. 2006. Microbiology 152:779-786) after administration of either (1) ZCR533, (2) ZCR533-CFA/I, or (3) ZCR533-CFA/I+mLT construct. The mucosal sample concentrations were determined from standard curves using purified mouse IgA and IgG antibody, and the CFA/I or LT-specific antibody concentrations were normalized based on total IgA and IgG content, with values expressed as µg CFA/I or LT-specific IgA or IgG/mg total IgA or IgG. Results are shown in FIGS. 2-29.

Example 3

CFA/I Binding Inhibition Assay

Figure 30:
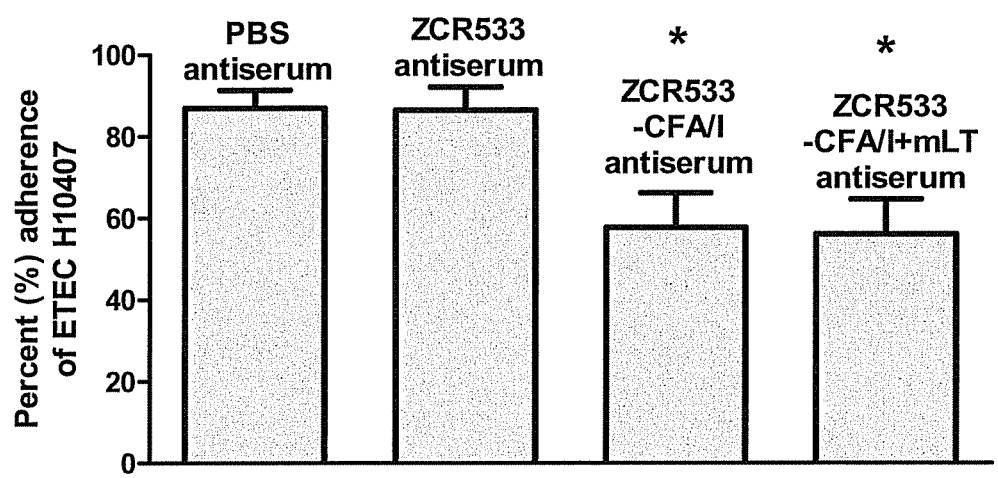
FIG. 30 shows inhibition of wild-type ETEC H10407 binding to Caco-2 cells by mouse antiserum generated against the ZCR533 EHEC vector, the ZCR533-CFA/I vaccine construct, or the ZCR533-CFA/I+mLT vaccine construct.

ETEC wild-type H10407 possessing CFA/I were used to assay for binding inhibition to Caco-2 cells. The Caco-2 cells were grown to confluence in a culture flask, trypsinized and distributed onto sterile chamber glass slides. ETEC bacteria ($1\times10^9$) were incubated with mouse serum raised against the ZCR533 vector, and the ZCR533-CFA/I and ZCR533-CFA/I plus mLT vaccine constructs, for 30 minutes. Anti-CFA/I and non-immune mouse serums were used as positive and negative controls, respectively. The bacterial mixture was added to the Caco-2 cells and incubated for 3 hours at 37° C. The Caco-2 cells were washed with PBS and fixed with 70% methanol for 10 minutes, and then the fixed cells were stained with 20% Giemsa stain (Sigma). The slide containing the Caco-2 cells and the ETEC H10407 bacteria were examined under a microscope at 400×-1,000× magnification and the percentage of Caco-2 cells with at least one adherent ETEC bacterial cell was determined. The results were averaged for three separate fields each with 50 Caco-2 cells per field. Results are shown in FIG. 30.

Example 4

LT Inhibition Assay

CHO Cell Elongation

Figure 31:
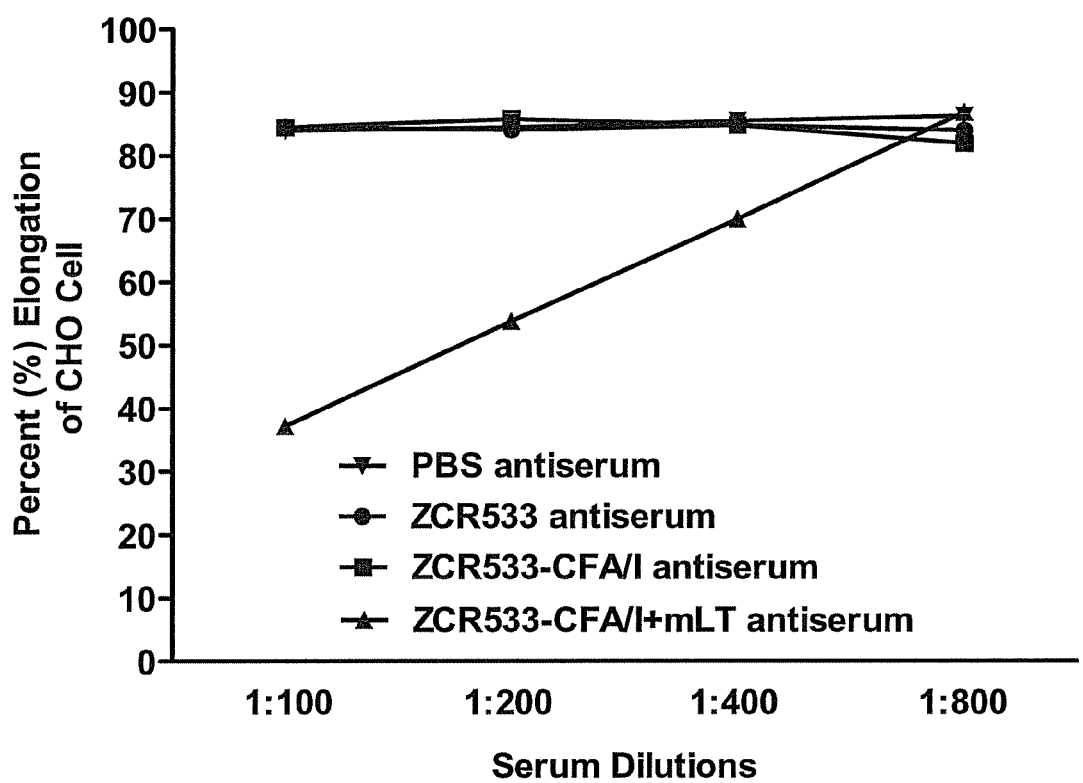
FIG. 31 shows inhibition of LT-mediated elongation of CHO cells by mouse antisera raised against the ZCR533 EHEC vector, the ZCR533-CFA/I vaccine construct, or the ZCR533-CFA/I+mLT vaccine construct.

LT inhibition was determined by measuring extent of Chinese hamster ovary (CHO-K1) cell elongation in the presence of LT essentially as previously described (Ranallo, R. T., et al., 2005. Infect. Immun. 73:258-267). LT (List) (25 ng) was incubated with mouse serum raised against the ZCR533 vector, the ZCR533-CFA/I vaccine construct, or the ZCR533-CFA/I+mLT vaccine construct, for 30 minutes. Toxin-antiserum mixtures were added to trypsinized CHO cells and assayed for elongation. Anti-LT and non-immune mouse serums were used as positive and negative controls, respectively. The results were averaged for three separate fields each with 100 CHO cells per field. CHO elongation with no LT was around 15% of the cells and with 25 ng LT around 90% of the cells. Results are shown in FIG. 31.

GM1 Inhibition Assay

Figure 32:
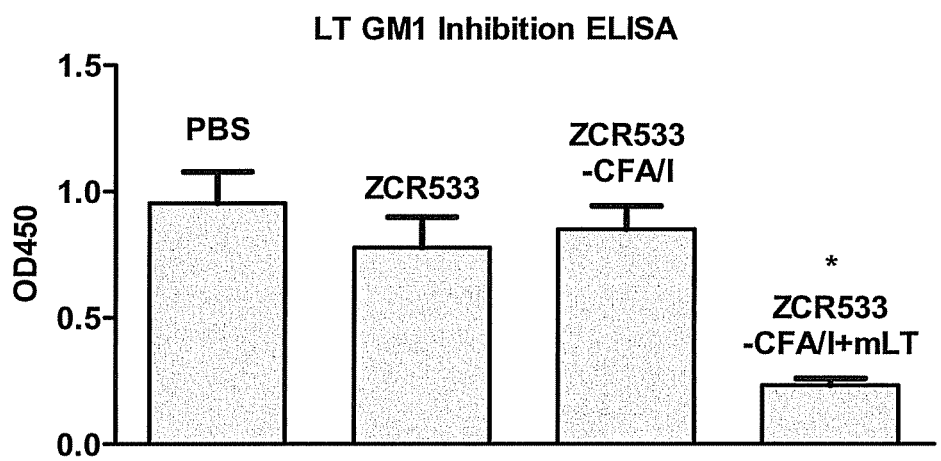
FIG. 32 shows inhibition of LT-binding to GM1 by mouse anti-serum against ZCR533 vector, ZCR533-CFA/I vaccine, or ZCR533-CFA/I+mLT vaccine strains.
Figure 33:
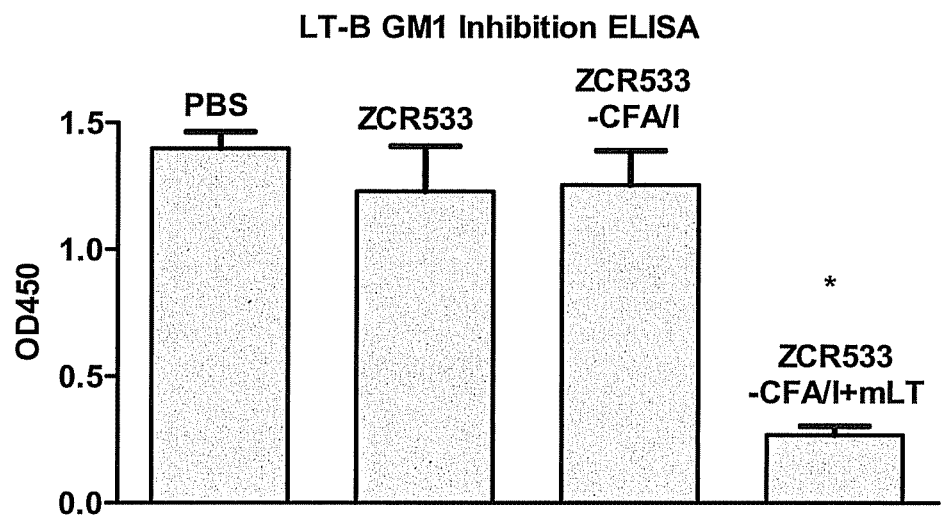
FIG. 33 shows inhibition of LT-B-binding to GM1 by mouse anti-serum against ZCR533 vector, ZCR533-CFA/I vaccine, or ZCR533-CFA/I+mLT vaccine strains.

LT inhibition was also determined by measuring extent of inhibition of LT and the B subunit of LT (LT-B) from binding to its GM1 receptor the presence of LT essentially as previously described (Moravec, T., 2006. Vaccine 25:1647-1657). LT (List) or LT-B (Sigma) were incubated with mouse serum raised against the ZCR533 vector, the ZCR533-CFA/I vaccine construct, or the ZCR533-CFA/I+mLT vaccine construct, for 30 minutes. Toxin-antiserum mixtures were added to wells of ELISA plates coated with GM1 and a standard ELISA performed. Anti-LT and non-immune mouse serums were used as positive and negative controls, respectively. Results are shown in FIG. 32 and FIG. 33.

Example 5

Active Immunization

Mice were vaccinated with two doses ($5\times10^7$ CFU/20 µl each dose) of the ZCR533 vector, ZCR533-CFA/I vaccine construct, or the ZCR533-CFA/I+mLT vaccine construct. The second dose was administered 14 days after the initial dose.

The vaccinated mice were intranasally challenged with a lethal dose of wild-type ETEC strain H10407 ($3\times10^9$ bacteria) in a volume of 25 µl 15 days following second vaccination. The mice were examined for mortality and morbidity at least twice daily for 14 days post challenge. The clinical signs of distress monitored were weight loss, ruffled fur, huddling, lethargy, shivering, labored breathing, difficulty in moving, refusal to eat or drink, diarrhea, drainage from eyes, shivering, hunched posture and moribund condition. Results are shown in Table 3.

TABLE 3

Active immunization

| Days | PBS Diluent | ZCR533 Vector Strain | CFA/I Vaccine Strain | CFA/I + mLT Vaccine Strain |
|---|---|---|---|---|
| 0 | 20/20 Alive | 20/20 Alive | 20/20 Alive | 20/20 Alive |
| 1 | 20/20 Alive | 20/20 Alive | 20/20 Alive | 20/20 Alive |
| 2 | 12/20 Alive | 12/20 Alive | 17/20 Alive | 18/20 Alive |
| 3 | 0/20 Alive | 0/20 Alive | 13/20 Alive | 13/20 Alive |
| 4 | 0/20 Alive | 0/20 Alive | 12/20 Alive | 11/20 Alive |
| 5 | 0/20 Alive | 0/20 Alive | 12/20 Alive | 11/20 Alive |
| % Survival | 0/20 0% Survival | 0/20 0% Survival | 12/20 60% Survival ($p < 0.05$ vs. sham mice) | 11/20 total 55% Survival ($p < 0.05$ vs. sham mice) |

Example 6

Passive Immunization

Mice were intranasally challenged with a lethal dose of wild-type ETEC strain H10407 ($3\times10^9$ bacteria/25) previously incubated for 1 hour with a 1:10 dilution of serum collected from mice vaccinated with two doses of either the ZCR533 vector, the ZCR533-CFA/I vaccine construct, or the ZCR533-CFA/I+mLT vaccine construct. The serum was prepared by vaccinating mice with two doses ($5\times10^7$ bacteria/20 µl, each dose, 14 days between doses) of either the ZCR533 vector, the ZCR533-CFA/I vaccine construct, or the ZCR533-CFA/I+mLT vaccine construct. 15 days after the second vaccination, the mice were sacrifice and bled, and the serum collected and prepared using standard methods. The serum was diluted ten-fold prior to being incubated with the ETEC strain H10407.

The mice challenged with serum-incubated ETEC strain H10407 were examined for mortality and morbidity at least twice daily for 14 days post challenge as described above for the assessment of active immunization. Results are shown in Table 4.

TABLE 4

Passive Immunization

| Days | PBS Diluent | ZCR533 Vector Strain | CFA/I Vaccine Strain | CFA/I + mLT Vaccine Strain |
|---|---|---|---|---|
| 0 | 10/10 Alive | 10/10 Alive | 10/10 Alive | 10/10 Alive |
| 1 | 10/10 Alive | 10/10 Alive | 10/10 Alive | 10/10 Alive |
| 2 | 2/10 Alive | 3/10 Alive | 8/10 Alive | 9/10 Alive |
| 3 | 0/10 Alive | 0/10 Alive | 6/10 Alive | 8/10 Alive |
| 4 | 0/10 Alive | 0/10 Alive | 6/10 Alive | 6/10 Alive |
| 5 | 0/10 Alive | 0/10 Alive | 6/10 Alive | 6/10 Alive |
| % Survival | 0/10 total 0% Survival | 0/10 0% Survival | 6/10 60% Survival | 6/10 60% Survival |

Example 7

Lung Clearance

Figure 34:
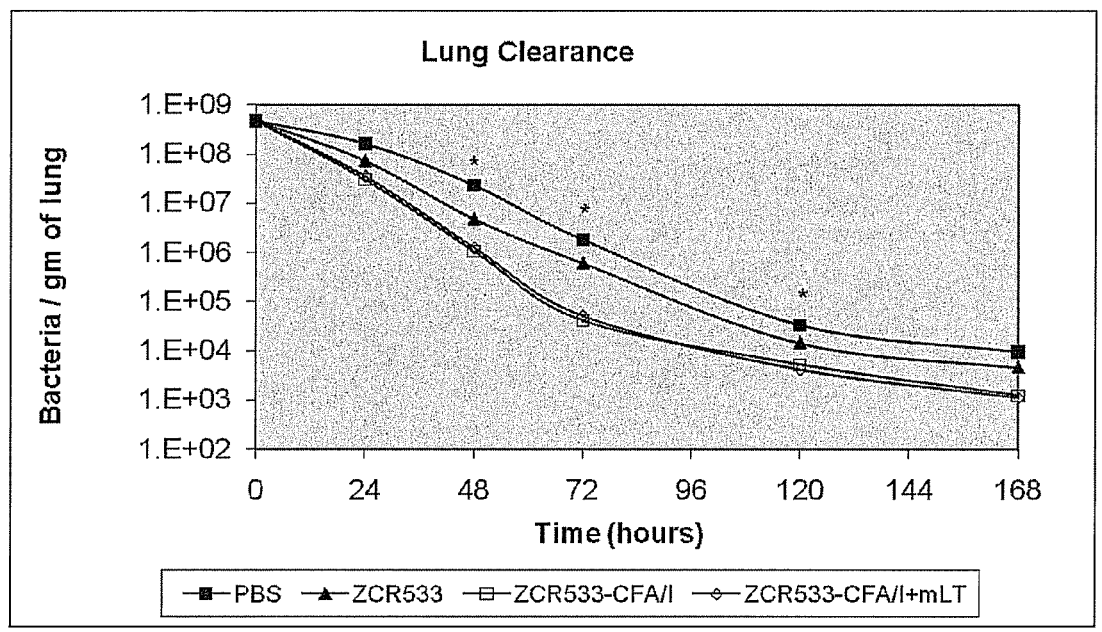
FIG. 34 shows clearance of intranasally administered wild-type ETEC H10407 from mouse lung after vaccination with the ZCR533 EHEC vector, the ZCR533-CFA/I vaccine construct, or the ZCR533-CFA/I+mLT vaccine construct. *P<0.05

Mice were vaccinated twice ($5\times10^7$ CFU/20 µl per vaccination, 14 days between vaccinations). 15 days after the second vaccination, the vaccinated mice were intranasally challenged with a sublethal dose of wild-type ETEC strain H10407 (approximately $1\times10^9$ bacteria) in a volume of 25 µl 15 days following immunization with the ZCR vector (ZCR), the ZCR533-CFA/I vaccine construct (CFA/I), or the ZCR533-CFA/I+mLT vaccine construct (mLT). The mice were euthanized, and the lungs aseptically removed and placed in 2 ml of sterile PBS. The lungs were homogenized using Potter-Elvehjem glass tissue grinders to free bacteria into suspension, and the homogenates plated to determine the number of bacteria present in the lungs at the indicated times (24, 48, 72, 120, and 168 hours) post challenge. Results are shown in FIG. 34.

Example 8

Bacterial colonization of the small intestines and intestinal fluid accumulation were measured in mice previously vaccinated with the ZCR533-CFA/I or ZCR533-CFA/I+mLT vaccine constructs. The ability of the vaccine constructs to induce an immune response in the mice sufficient to significantly reduce ETEC H10407 bacterial colonization of the small intestines and reduce intestinal fluid accumulation induced by the LT alone or ETEC H10407 bacteria was measured. The mice were either vaccinated intranasally (as described above) (two doses, 14-day interval between doses, $5\times10^7$ bacteria/20 µl per dose) or intragastrically (one dose given daily for three consecutive days, repeated three times with a 14-day interval between each three consecutive days dosing, $3\times10^9$ bacteria/200 µl per dose). Each mouse was intragastrically administered using a 20-gauge ball-tip needle 100 µl sterile 10% sodium bicarbonate. Thirty minutes later a suspension of either vaccine construct ($3\times10^9$ bacteria) in a volume of 200 µl was intragastrically administered to the mice.

Bacterial Colonization.

Figure 35:
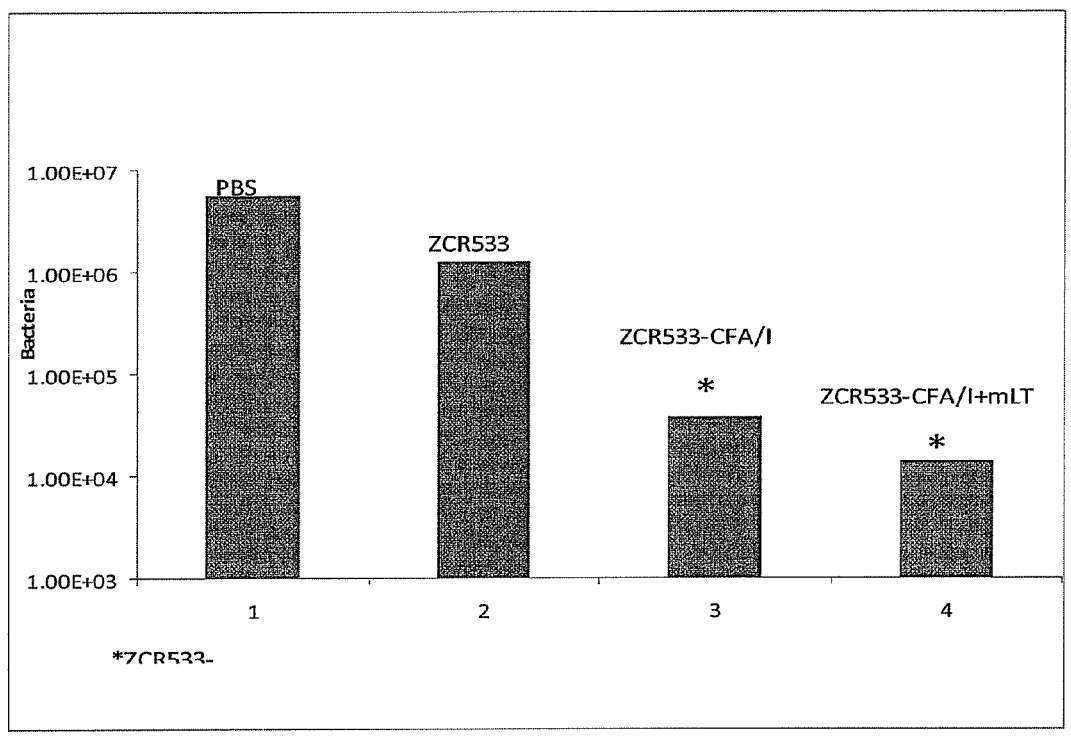
FIG. 35 shows inhibition of wild-type ETEC H10407 colonization of the small intestine after intranasal vaccination with the ZCR533 EHEC vector, the ZCR533-CFA/I vaccine construct, or the ZCR533-CFA/I+mLT vaccine construct.
Figure 36:
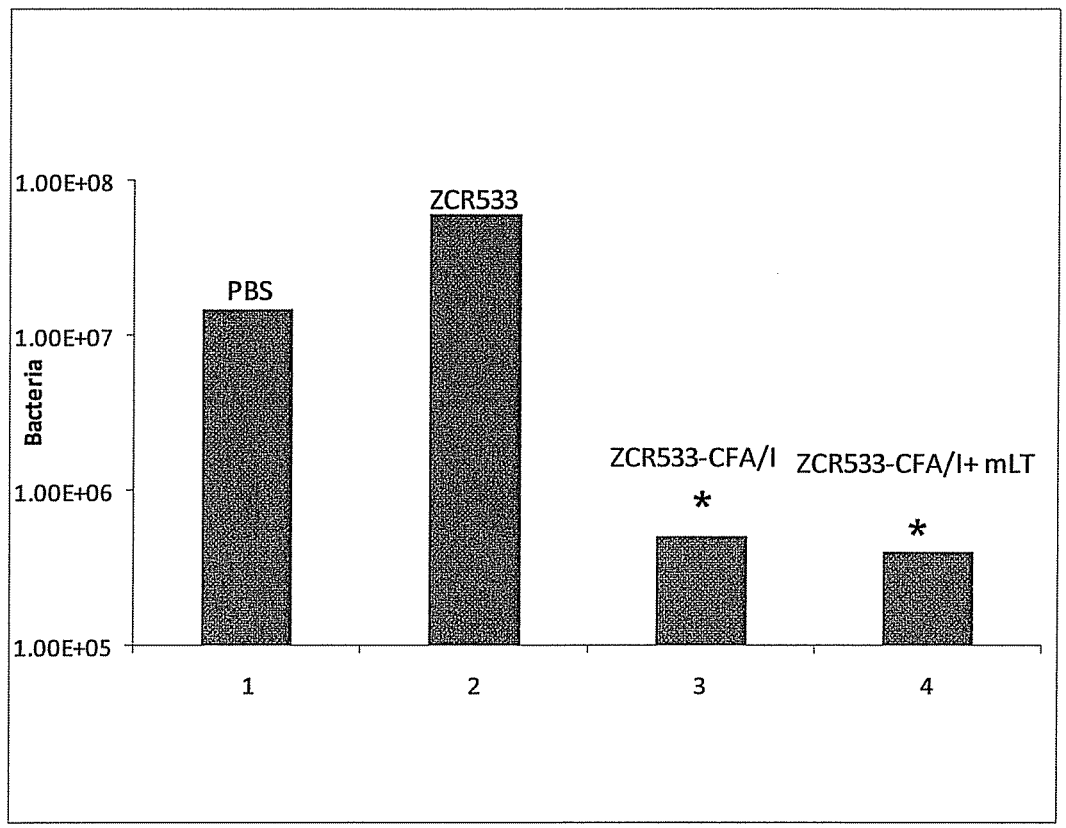
FIG. 36 shows inhibition of wild-type ETEC H10407 colonization of the small intestine after intragastric vaccination with the ZCR533 EHEC vector, the ZCR533-CFA/I vaccine construct, or the ZCR533-CFA/I+mLT vaccine construct.

Vaccinated mice received sterile drinking water containing streptomycin (5 g/liter) 72 hours prior to ETEC H10407 intragastric administration to eradicate normal resident flora in the intestinal tract. The streptomycin-treated water contained 5% fructose to encourage water consumption. Streptomycin-treated water was replaced with sterile normal water (no streptomycin) 6 hours prior to ETEC H10407 inoculation. Each mouse was intragastrically administered using a 20-gauge ball-tip needle 100 µl sterile 10% sodium bicarbonate. Thirty minutes later a suspension of ETEC H10407 ($3\times10^9$ bacteria) in a volume of 300 tad was intragastrically administered to the mice. Mice were euthanized 24 hours following ETEC H10407 inoculation and ETEC H10407 bacteria harvested from the small intestines. The small intestines were aseptically removed and placed into 2 ml of sterile 5% saponin solution, vortexed for 5-10 seconds, incubated for 10 minutes at room temperature and vortexed a second time for 5-10 seconds. The small intestines were homogenized using Potter-Elvehjem glass tissue grinders to free bacteria into suspension. The resulting suspensions were plated to determine the number of bacteria present in the small intestines of each mouse. Results after intranasal vaccination are shown in FIG. 35. Results after intragastric vaccination are shown in FIG. 36.

Fluid Accumulation (LT)

Figure 37:
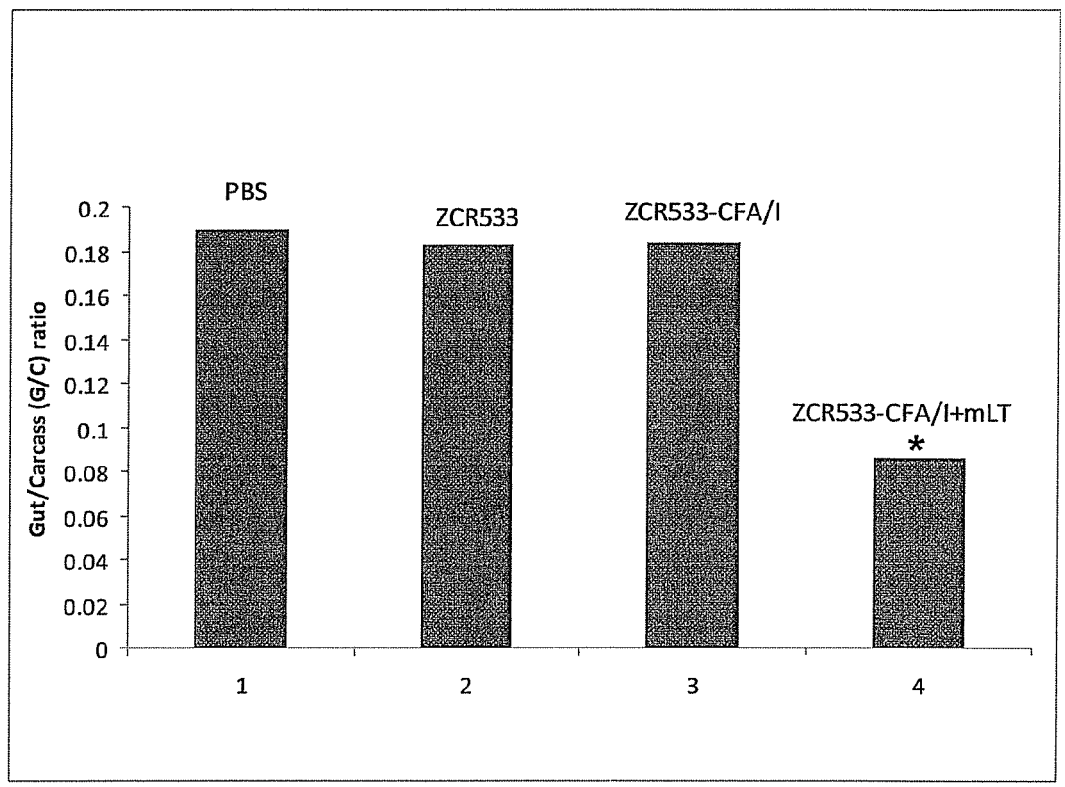
FIG. 37 shows inhibition of intestinal fluid accumulation after intragastric vaccination with the ZCR533 EHEC vector, the ZCR533-CFA/I vaccine construct, or the ZCR533-CFA/I+mLT vaccine construct, then intragastric administration of heat-labile enterotoxin (25 µg).

Vaccinated mice were intragastrically administered using a 20-gauge ball-tip needle 100 µl sterile 10% sodium bicarbonate. Thirty minutes later a suspension of LT (25 µg) in a volume of 400 µl was intragastrically administered to the mice. Mice were euthanized 3 hours following LT administration and the entire intestines (from duodenum to anus) were carefully removed to retain any accumulated fluid. Fluid accumulation was determined by weighing the intestines. The carcass was weighted separately and a gut/carcass ratio was determined for each mouse. Results are shown in FIG. 37.

Fluid Accumulation (ETEC)

Figure 38:
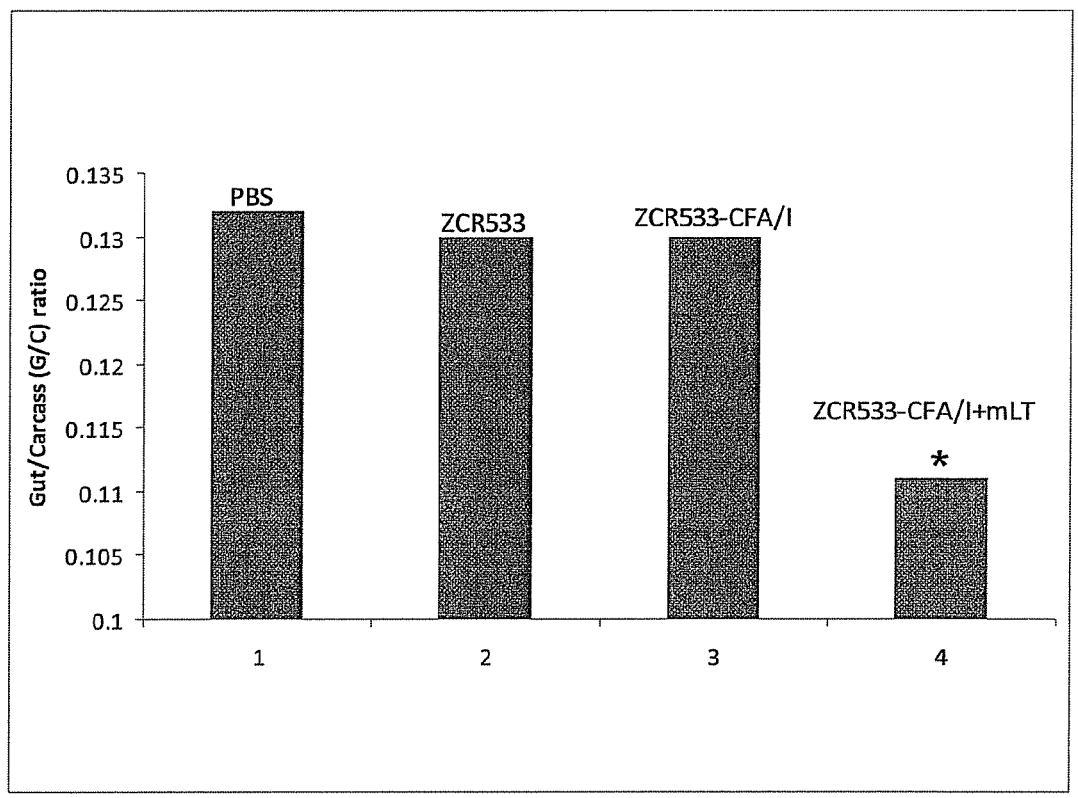
FIG. 38 shows inhibition of intestinal fluid accumulation after intragastric vaccination with the ZCR533 EHEC vector, the ZCR533-CFA/I vaccine construct, or the ZCR533-CFA/I+mLT vaccine construct, then administration of wild-type ETEC H10407.

Vaccinated mice were intragastrically administered using a 20-gauge ball-tip needle 100 µl sterile 10% sodium bicarbonate. Thirty minutes later a suspension of ETEC H10407 ($3\times10^9$ bacteria) in a volume of 300 µl intragastrically administered to the mice. Mice were euthanized 3 hours following ETEC H10407 administration and the entire intestines (from duodenum to anus) were carefully removed to retain any accumulated fluid. Fluid accumulation was determined by weighing the intestine's. The carcass was weighted separately and a gut/carcass ratio was determined for each mouse. Results are shown in FIG. 38.

Example 9

Mice are vaccinated with two doses ($5\times10^7$ CFU/20 µl each dose) of the ZCR533 vector. The second dose was administered 14 days after the initial dose. 15 days after the second vaccination, the vaccinated mice were intranasally challenged with a sublethal dose of wild-type EHEC strain (approximately $1\times10^9$ bacteria).

Active immunization is assessed as described in Example 5. Mice vaccinated with the ZRC533 vector will exhibit improved protection against wild-type EHEC challenge compared to the negative control.

Passive immunization is assessed as described in Example 6. Mice challenged with a lethal dose of wild-type EHEC strain ($3\times10^9$ bacteria/25 µl) previously incubated for 1 hour with a 1:10 dilution of serum collected from mice vaccinated with two doses of the ZCR533 vector will exhibit improved protection compared to the negative control.

Lung Clearance is assessed as described in Example 7. The lungs of mice vaccinated with the ZCR533 vector will have fewer EHEC bacteria than unvaccinated mice.

Bacterial colonization is assessed as described in Example 8. The small intestines of mice vaccinated with the ZCR533 vector will exhibit reduced EHEC colonization compared to unvaccinated mice.

The complete disclosure of all patents, patent applications, and publications, and electronically available material cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of generating an antibody response in a mammalian subject against a mutant heat-labile toxin (LT) of an enterotoxigenic *E. coli* (ETEC) and a heterologous microbial immunogen, the method comprising administration to said subject, a composition comprising an attenuated enterohemorrhagic *E. coli* (EHEC) in an amount effective to induce the antibody response, wherein the attenuated EHEC is modified to comprise: (a) truncation of the intimin adhesin by a mutation of the coding region of its eae gene at the locus of enterocyte effacement (LEE); (b) a plasmid expressing the mutant LT, and (c) a plasmid expressing the heterologous microbial antigen, wherein the mutant LT is expressed in the periplasmic space.

2. The method of claim 1, wherein the administration is intranasal administration.

3. The method of claim 1, wherein the heterologous microbial immunogen is the colonization factor antigen I (CFA/I) of an enterotoxigenic *E. coli* (ETEC).

4. The method of claim 2, wherein the antibody response generated in the subject is a serum antibody response and a mucosal antibody response against a wild-type ETEC and a wild-type EHEC.

5. The method of claim 4, wherein the antibody response protects the subject against a challenge infection by a wild-type ETEC.

6. The method of claim 4, wherein the antibody response protects the subject against a challenge infection by a wild-type EHEC.

* * * * *